(12) United States Patent
Leder et al.

(10) Patent No.: US 8,293,701 B2
(45) Date of Patent: Oct. 23, 2012

(54) METHODS AND COMPOSITIONS RELATING TO A VACCINE AGAINST PROSTATE CANCER

(75) Inventors: Christoph Leder, Wendisch Evern (DE); Alan D. King, Highland, MD (US); Maxim Pavlenko, Moscow (RU); Pavel Pisa, Basel (SE)

(73) Assignee: Cellectis S.A., Paris (FR)

( * ) Notice: Subject to any disclaimer, the term of this patent is extended or adjusted under 35 U.S.C. 154(b) by 638 days.

(21) Appl. No.: 11/922,633

(22) PCT Filed: Jun. 21, 2006

(86) PCT No.: PCT/US2006/024076
§ 371 (c)(1),
(2), (4) Date: Feb. 12, 2009

(87) PCT Pub. No.: WO2007/002149
PCT Pub. Date: Jan. 4, 2007

(65) Prior Publication Data
US 2010/0047260 A1 Feb. 25, 2010

Related U.S. Application Data

(60) Provisional application No. 60/692,238, filed on Jun. 21, 2005.

(51) Int. Cl.
*A01N 37/18* (2006.01)
(52) U.S. Cl. .......................................... 514/1.1; 514/19.5
(58) Field of Classification Search ........................ None
See application file for complete search history.

(56) References Cited

U.S. PATENT DOCUMENTS 7,767,387 B2 * 8/2010 Morris et al. ...................... 435/4
2006/0140965 A1 * 6/2006 Cassart et al. .............. 424/185.1

OTHER PUBLICATIONS

Ben-Efraim, Tumor Biology 1999; 20: 1-24.*
Frazer, I., Expert. Opin. Pharmacother. 2004; 5: 2427-2434.*
Granziero et al. Eur. J. Immunol. 1999, 29:1127-1138.*
Byers, T., CA Journal, vol. 49, No. 6, Nov./Dec. 1999.*
"Prostate-Specific Antigen (Psa)", Encyclopedia of Public Health | 2002 | Malkowicz, S. Bruce | 700+ words | http://www.encyclopedia.com/doc/1G2-3404000694.html.
"PSA", McGraw-Hill Concise Dictionary of Modern Medicine. c 2002 by The McGraw-Hill Companies, Inc. online at http://medical-dictionary.thefreedictionary.com/PSA.
"Definition of Therapeutic hiv vaccine", p. 1 of 4 online at http://dictionary.babylon.com/therapeutic_hiv_vaccine/.
"Therapeutic Vaccine (Treatment Vaccine)" online at http://treasuresoftheinternet.org/dictionary/aids/t/th/therapeutic_vaccine.shtml.
"Cell Therapy aka Therapeutic "Vaccine" Suprise Announcement for World AIDS Day", By Mike Barr, Dec. 2004, http://forums.poz.com/index.php?topic=29858.0.
"Therapeutic vaccines: Realities of today and hopes for tomorrow" by Michael Sela and Maurice R. Hilleman, in the Proceedings of the National Academy of Sciences of the United States of America, and published in print PNAS, Oct. 5, 2004, vol. 101, No. Suppl 2 14559. online at http://www.pnas.org/content/101/suppl.2/14559.full.
"Looking at vaccines in cancer" online at p. 1 of 4 http://www.medical-explorer.com/cancer.php?028.
"treatment" (trtmnt) The american Heritager Medical Dictionary Copyright c 2007, 2004 by Houghton Mifflin Company. Published by Houghton Mifflin Company. All rights reserved. online at p. 1 of 5 at http://medical-dictionary.thefreedictionary.com/treatment.
"Prostate Cancer Treatment (PDQ)", "Treatment Option Overview", online at http://www.cancer.gov/cancertopics/pdq/treatment/prostate/Patient/page4.
"Prostate Cancer Treatment (PDQ)", "Treatment Options by Stage", online at http://www.cancer.gov/cancertopics/pdq/treatment/prostate/Patient/page5.
"Prostate Cancer Treatment (PDQ)", "Treatment Options for Recurrent Prostate Cancer" online at http://www.cancer.gov/cancertopics/pdq/treatment/prostate/Patient/page6.
NIH Public Access, Author Transcript, published in final edited form as: *Prostate*. 2008 Oct. 1; 68(14): 1546-1554.doi:10.1002/pros.20814.

* cited by examiner

*Primary Examiner* — Peter J Reddig
*Assistant Examiner* — Mark Halvorson
(74) *Attorney, Agent, or Firm* — Marvin S. Towsend

(57) ABSTRACT

An object of the invention is to provide methods and compositions relating to a vaccine against prostate cancer which includes a non-human-primate PSA for administration to humans to provide an immune response against human PSA. More generally, an object of the invention is to provide methods and compositions relating to using a non-human primate xenogeneic antigen (e.g. protein) in a human, wherein, with respect to the non-human primate xenogeneic antigen that is used, there are relatively few interspecies differences between the non-human primate xenogeneic antigen and the human self antigen in order to induce an optimal immune response in the human to its native self antigen.

4 Claims, 6 Drawing Sheets

DNA Sequence Comparison

|  |  | 10 |  | 20 |  | 30 |  | 40 |  |
|---|---|---|---|---|---|---|---|---|---|
| Human PSA |  | ggggg | agccc | caago | ttacc | acctg | caccc | ggaga | gctgt | 40 |
| Mmulatta P |  |  |  | c | tcacc | gcctg | cacoc | ggaca | gctgt | 26 |
| Mfascicula |  |  |  | gc | tcacc | gcctg | cacct | ggaca | gctgt | 27 |
| Consensus |  |  |  | gC | TcACC | gCCTG | CACCt | GGAcA | GCTGT |  |

|  |  | 50 |  | 60 |  | 70 |  | 80 |  |
|---|---|---|---|---|---|---|---|---|---|
| Human PSA | gtcac | catgt | gggtc | ccggt | tgtct | tcctc | accct | gtccg | 80 |
| Mmulatta P | gtcac | catgt | ggptt | ctggt | tgtct | tcctc | accct | gtccg | 66 |
| Mfascicula | gtcac | catgt | ggptt | ctggt | tgtct | tcctc | accct | gtccg | 67 |
| Consensus | GTCAC | CATGT | GGGTt | CtGGT | TGTCT | TCCTC | ACCCT | GTCCG |  |

↑start

|  |  | 90 |  | 100 |  | 110 |  | 120 |  |
|---|---|---|---|---|---|---|---|---|---|
| Human PSA | tgacg | tggat | tggtg | ctgca | cccct | catcc | tgtct | cggat | 120 |
| Mmulatta P | tgacg | tggat | tggcg | ctgca | cccct | catcc | tgtct | cggat | 106 |
| Mfascicula | tgacg | tggat | tggcg | ctgca | cccct | catcc | tgtct | cggat | 107 |
| Consensus | TGACG | TGGAT | TGGcG | CTGCA | CCCCT | CATCC | TGTCT | CGGAT |  |

|  |  |  |  |  |  |  |  |  |  |
|---|---|---|---|---|---|---|---|---|---|
| Human PSA | tgtgg | gaggc | tggga | gtgcg | agaag | cattc | ccaac | cctgg | 160 |
| Mmulatta P | tgtgg | gaggc | tggga | gtgcg | agaag | cattc | ccaac | cctgg | 146 |
| Mfascicula | tgtgg | gaggc | tggga | gtgcg | agaag | cattc | ccaac | cctgg | 147 |
| Consensus | TGTGG | GAGGC | TGGGA | GTGCG | AGAAG | CATTC | CCAAC | CCTGG |  |

|  |  | 170 |  | 180 |  | 190 |  | 200 |  |
|---|---|---|---|---|---|---|---|---|---|
| Human PSA | caggt | gcttg | tggcc | tctcg | tggca | gggca | gtctg | cggcg | 200 |
| Mmulatta P | caggt | gcttg | tggcc | tctcg | tggca | gggca | gtctg | cgggg | 186 |
| Mfascicula | caggt | gcttg | tggcc | tctca | tggca | gggca | gtctg | cgggg | 187 |
| Consensus | CAGGT | GCTTG | TGGCC | TCTCg | TGGCA | GGGCA | GTCTG | CGGGg |  |

|  |  | 210 |  | 220 |  | 230 |  | 240 |  |
|---|---|---|---|---|---|---|---|---|---|
| Human PSA | gtgtt | ctggt | gcacc | cccag | tgggt | cctca | cagct | gccca | 240 |
| Mmulatta P | gtgtt | ctggt | gcacc | cccag | tgggt | cctca | cagct | gccca | 226 |
| Mfascicula | gtgtt | ctggt | gcacc | cccag | tgggt | gctca | cagct | gccca | 227 |
| Consensus | GTGTT | CTGGT | GCACC | CCCAG | TGGGT | cCTCA | CAGCT | GCCCA |  |

|  |  | 250 |  | 260 |  | 270 |  | 280 |  |
|---|---|---|---|---|---|---|---|---|---|
| Human PSA | ctgca | tcagg | aacaa | aagcg | tgatc | ttgct | gggtc | ggcao | 280 |
| Mmulatta P | ctgca | tcagg | agcaa | cagcg | tgatc | ttgct | gggtc | ggcao | 266 |
| Mfascicula | ctgca | tcagg | agcca | cagcg | tgatc | ttgct | gggtc | ggcao | 267 |
| Consensus | CTGCA | TCAGG | AgCaA | cAGCG | TGATC | TTGCT | GGGTC | GGCAC |  |

|  |  | 290 |  | 300 |  | 310 |  | 320 |  |
|---|---|---|---|---|---|---|---|---|---|
| Human PSA | agcct | gtttc | atcct | gaaga | cacag | gccag | gtatt | tcagg | 320 |
| Mmulatta P | aaccc | gtatt | atcct | gaaga | cacgg | gccag | gtgtt | tcagg | 306 |
| Mfascicula | aaccc | gtatt | atcct | gaaga | cacgg | gccag | gtgtt | tcagg | 307 |
| Consensus | AaCCc | GTaTt | ATCCT | GAAGA | CACgG | GCCAG | GTgTT | TCAGG |  |

FIG. 1A

DNA Sequence Comparison

| | | 330 | | 340 | | 350 | | 360 | |
|---|---|---|---|---|---|---|---|---|---|
| Human PSA | tcagc | cacag | cttcc | cacac | ccgct | ctacg | atatg | agcct | 360 |
| Mmulatta P | tcagc | cacag | cttcc | cacac | ccgct | ctaca | atatg | agcct | 346 |
| Mfascicula | tcagc | cacag | cttcc | cacac | ccgct | ctaca | atatg | agcct | 347 |
| Consensus | TCAGC | CACAG | CTTCC | CACAC | CCGCT | CTACa | ATATG | AGCCT | |

| | | 370 | | 380 | | 390 | | 400 | |
|---|---|---|---|---|---|---|---|---|---|
| Human PSA | cctga | agaat | cgatt | cctca | ggcca | ggtga | tgact | ccagc | 400 |
| Mmulatta P | cctga | agaat | cgata | cctcg | ggcca | ggtga | tgact | ccagc | 386 |
| Mfascicula | cctga | agaat | cgata | cctcg | ggcca | ggtga | tgact | ccagc | 387 |
| Consensus | CCTGA | AGAAT | CGATa | CCTCg | GGCCA | GGTGA | TGACT | CCAGC | |

| | | 410 | | 420 | | 430 | | 440 | |
|---|---|---|---|---|---|---|---|---|---|
| Human PSA | cacga | cctca | tgctg | ctccg | cctgt | cagag | cctgc | cgagc | 440 |
| Mmulatta P | cacga | cctca | tgctg | ctccg | cctgt | cagag | cctgc | cgaga | 426 |
| Mfascicula | cacga | cctca | tgctg | ctccg | cctgt | cagag | cctgc | cgaga | 427 |
| Consensus | CACGA | CCTCA | TGCTG | CTCCG | CCTGT | CAGAG | CCTGC | CGAGa | |

| | | 450 | | 460 | | 470 | | 480 | |
|---|---|---|---|---|---|---|---|---|---|
| Human PSA | tcacg | gatgc | tgtga | aggtc | atgga | cctgc | ccacc | cagga | 480 |
| Mmulatta P | tcaca | gatgc | tgtgc | aggtc | ctgga | cctgc | ccacc | tggga | 466 |
| Mfascicula | tcaca | gatgc | tgtgc | aggtc | ctgga | cctgc | ccacc | tggga | 467 |
| Consensus | TCACa | GATGC | TGTGc | AGGTC | cTGGA | CCTGC | CCACC | tgGGA | |

| | | 490 | | 500 | | 510 | | 520 | |
|---|---|---|---|---|---|---|---|---|---|
| Human PSA | gccag | cactg | gggac | cacct | gctac | gcctc | aggct | gggc | 520 |
| Mmulatta P | gccag | agctg | gggac | cacgt | gctac | gcctc | aggct | ggggc | 506 |
| Mfascicula | gccag | agctg | gggac | cacgt | gctac | gcctc | aggct | gggc | 507 |
| Consensus | GCCAG | agCTG | GGGAC | CACgT | GCTAC | GCCTC | AGGCT | GGGGC | |

| | | 530 | | 540 | | 550 | | 560 | |
|---|---|---|---|---|---|---|---|---|---|
| Human PSA | agcat | tgaac | cagag | gagtt | cttga | cccca | aagaa | acttc | 560 |
| Mmulatta P | agcat | cgaac | cagag | gaaca | cttga | ctcca | aagaa | acttc | 546 |
| Mfascicula | agcat | cgaac | cagag | gaaca | cttga | ctcca | aagaa | acttc | 547 |
| Consensus | AGCAT | cGAAC | CAGAG | GAaca | CTTGA | CtCCA | AAGAA | ACTTC | |

| | | 570 | | 580 | | 590 | | 600 | |
|---|---|---|---|---|---|---|---|---|---|
| Human PSA | agtgt | gtgga | cctcc | atgtt | atttc | caatg | acgtg | tgtgc | 600 |
| Mmulatta P | agtgt | gtgga | cctcc | atatt | atttc | caatg | atgtg | tgtgc | 586 |
| Mfascicula | agtgt | gtgga | cctcc | atatt | atttc | caatg | atgtg | tgtgc | 587 |
| Consensus | AGTGT | GTGGA | CCTCC | ATaTT | ATTTC | CAATG | AtGTG | TGTGC | |

| | | 610 | | 620 | | 630 | | 640 | |
|---|---|---|---|---|---|---|---|---|---|
| Human PSA | gcaag | ttcac | cctca | gaagg | tgacc | aagtt | catgc | tgtgt | 640 |
| Mmulatta P | gcaag | ttcac | tctca | gaagg | tgacc | aagtt | catgc | tgtgt | 626 |
| Mfascicula | gcaag | ttcac | tctca | gaagg | tgacc | aagtt | catgc | tgtgt | 627 |
| Consensus | GCAAG | TTCAC | tCTCA | GAAGG | TGACC | AAGTT | CATGC | TGTGT | |

FIG. 1B

DNA Sequence Comparison

|  | 650 |  | 660 |  | 670 |  | 680 |  |
|---|---|---|---|---|---|---|---|---|
| Human PSA | gctgg | acgct | ggaca | ggggg | caaaa | gcacc | tgctc | gggtg | 680 |
| Mmulatta P | gctgg | acgct | ggatg | ggcgg | caaaa | gcacc | tgctc | gggtg | 666 |
| Mfascicula | gctgg | acgct | ggatg | ggcgg | caaaa | gcacc | tgctc | gggtg | 667 |
| Consensus | GCTGG | ACGCT | GGAtg | GGcGG | CAAAA | GCACC | TGCTC | GGGTG |  |

|  | 690 |  | 700 |  | 710 |  | 720 |  |
|---|---|---|---|---|---|---|---|---|
| Human PSA | attct | ggggg | cccac | ttgtc | tgtaa | tggtg | tgctt | caagg |  |
| Mmulatta P | attct | ggggg | cccac | tggtc | tgtga | cggtg | tgctt | caagg | 720 |
| Mfascicula | attct | ggggg | cccac | tggtc | tgtga | cggtg | tgctt | caagg | 706 |
| Consensus | ATTCT | GGGGG | CCCAC | TgGTC | TGTgA | cGGTG | TGCTT | CAAGG | 707 |

|  | 730 |  | 740 |  | 750 |  | 760 |  |
|---|---|---|---|---|---|---|---|---|
| Human PSA | tatca | cgtca | tgggg | cagtg | aacca | tgtgc | cctgc | ccgaa | 760 |
| Mmulatta P | tatca | cgtca | tgggg | cagtc | aacca | tgtgc | cctgc | cccga | 746 |
| Mfascicula | tatca | cgtca | tgggg | cagtc | aacca | tgtgc | cctgc | cccga | 747 |
| Consensus | TATCA | CGTCA | TGGGG | CAGTc | AACCA | TGTGC | CCTGC | CCcgA |  |

|  | 770 |  | 780 |  | 790 |  | 800 |  |
|---|---|---|---|---|---|---|---|---|
| Human PSA | aggcc | ttccc | tgtac | accaa | ggtgg | tgcat | taccg | gaagt | 800 |
| Mmulatta P | aggcc | ttccc | tgtac | accaa | ggtgg | tgcgt | taccg | gaagt | 786 |
| Mfascicula | aggcc | ttccc | tgtac | accaa | ggtgg | tgcgt | taccg | gaagt | 787 |
| Consensus | AGGCC | TTCCC | TGTAC | ACCAA | GGTGG | TGCgT | TACCG | GAAGT |  |

|  | 810 |  | 820 |  | 830 |  | 840 |  |
|---|---|---|---|---|---|---|---|---|
| Human PSA | ggatc | aagga | cacca | tcgtg | gccaa | ccccT | gagca | ccct | 840 |
| Mmulatta P | ggatc | cagga | cacca | tcatg | gcaaa | cccct | gagca | cccc- | 825 |
| Mfascicula | ggatc | cagga | cacca | tcatg | gcaaa | cccct | gagca | cccc- | 826 |
| Consensus | GGATC | cAGGA | CACCA | TCaTG | GCaAA | CCCCT | GAGCA | CCCC |  |

|  | 850 |  | 860 |  | 870 |  | 880 |  |
|---|---|---|---|---|---|---|---|---|
| Human PSA | atcaa | ctccc | ta-tt | gtagt | -aaa- | ----- | ----- | ----- | 862 |
| Mmulatta P | atcaa | ctccc | taatt | gtagc | gaaaa | aaaaa | agtcc | acctc | 865 |
| Mfascicula | atcaa | ctccc | tactt | gtagc | gaaaa | aaaaa | a-tcc | acctc | 865 |
| Consensus | ATCAA | CTCCC | TA TT | GTAGc | gAAAa | aaaaa | a tcc | acctc |  |

|  | 890 |  | 900 |  | 910 |  | 920 |  |
|---|---|---|---|---|---|---|---|---|
| Human PSA | ----- | ----- | ----- | ----- | ----- | ----- | ----- | ----c | 863 |
| Mmulatta P | aagtt | cttgg | catca | tttgg | ctatt | ctaga | cacca | ggcac | 905 |
| Mfascicula | aagtt | ctg-g | catca | tttgg | ctatt | ctaga | cacca | ggcac | 904 |
| Consensus | aagtt | ct g | catca | tttgg | ctatt | ctaga | cacca | ggcaC |  |

|  | 930 |  | 940 |  | 950 |  | 960 |  |
|---|---|---|---|---|---|---|---|---|
| Human PSA | ttgga | acctt | ggaaa | tgacc | aggcc | aagac | tcagg | cctcc | 903 |
| Mmulatta P | ttgga | acctt | ggaaa | tgacc | gggcc | aaggc | tcaag | cctcc | 945 |
| Mfascicula | ttgga | acctt | ggaaa | tgacc | gggcc | aaggc | tcaag | cctcc | 944 |
| Consensus | TTGGA | ACCTT | GGAAA | TGACC | gGGCC | AAGgC | TCAaG | CCTCC |  |

FIG. 1C

*Rhesus* and Human PSA cDNA
Protein and DNA Sequence of huPSA and rhPSA
Protein sequence: 261 aa
DNA sequence: 786 nucleotides rhPSA
1 mut compared to published (plus one silent in nucleotide sequence):
mwvlvvfltl svtwigaapl ilsrivggwe cekhsqpwqv lvasrgravc ggvlvhpqwv
ltaahcirsn svillgrhnp yypedtgqvf qvshsfphpl ynmsllknry lgpgddsshd
lmlirlsepa eitdavqvld lptwepelgt tcyasgwgsl epeehltpkk lqcvdlhiis
ndvcaqvhsq kvtefmlcag swmggkstcs gdsggplvcd gvlqgitswg sqpcalpnrp
slytkvvryr kwiqdtiman p huPSA
mwvpvvfltl svtwigaapl ilsrivggwe cekhsqpwqv lvasrgravc ggvlvhpqwv
ltaahclmk svillgrhsl fhpedtgqvf qvshsfphpl ydmsllknrf lrpgddsshd
lmlirlsepa eitdavkvmd lptqepalgt tcyasgwgsi epeefltpkk lqcvdlhvis
ndvcaqvhpq kvtkfmlcag rwtggkstcs gdsggplvcn gvlqgitswg sepcalperp
slytkvvhyr kwikdtivan p rhPSA Genebank Accession # X73560
ATGTGGGTTCTGGTTGTCTTCCTCACCCTGTCCGTGACGTGGATTGGCGCTGCACCCCT
CATCCTGTCTCGGATTGTGGGAGGCTGGGAGTGCGAGAAGCATTCCCAACCCTGGCAGGT
GCTTGTGGCCTCTCGTGGCAGGGCAGTCTGTGGGGGTGTTCTGGTGCACCCCCAGTGGGT
CCTCACAGCTGCCCACTGCATCAGGAGCAACAGCGTGATCTTGCTGGGTCGGCACAACCC
GTATTATCCTGAAGACACGGGCCAGGTGTTTCAGGTCAGCCACAGCTTCCCACACCCGCT
CTACAACATGAGCCTCCTGAAGAATCGATACCTCGGGCCAGGTGATGACTCCAGCCACGA
CCTCATGCTGCTCCGCCTGTCAGAGCCTGCCGAGATCACAGATGCTGTGCAGGTCCTGGA
CCTGCCCACCTGGGAGCCAGAGCTGGGGACCACGTGCTACGCCTCAGGCTGGGGCAGCAT
CGAACCGGAGGAACACTTGACTCCAAAGAAACTTCAGTGTGTGGACCTCCATATTATTTC
CAATGATGTGTGTGCGCAAGTTCACTCTCAGAAGGTGACCGAGTTCATGCTGTGTGCTGG
AAGCTGGATGGGCGGCAAAAGCACCTGCTCGGGTGATTCTGGGGGCCCACTGGTCTGTGA
CGGTGTGCTTCAAGGTATCACGTCATGGGGCAGTCAACCATGTGCCCTACCCCGAAGGCC
TTCCCTGTACACCAAGGTGGTGCGTTACCGGAAGTGGATCCAGGACACCATCATGGCAAA
CCCCTGA huPSA Genebank Accession # X07730
ATGTGGGTCCCGGTTGTCTTCCTCACCCTGTCCGTGACGTGGATTGGTGCTGCACCCCTC
ATCCTGTCTCGGATTGTGGGAGGCTGGGAGTGCGAGAAGCATTCCCAACCCTGGCAGGTG
CTTGTGGCCTCTCGTGGCAGGGCAGTCTGCGGCGGTGTTCTGGTGCACCCCCAGTGGGTC
CTCACAGCTGCCCACTGCATCAGGAACAAAAGCGTGATCTTGCTGGGTCGGCACAGCCTG
TTTCATCCTGAAGACACAGGCCAGGTATTTCAGGTCAGCCACAGCTTCCCACACCCGCTC
TACGATATGAGCCTCCTGAAGAATCGATTCCTCAGGCCAGGTGATGACTCCAGCCACGAC
CTCATGCTGCTCCGCCTGTCAGAGCCTGCCGAGCTCACGGATGCTGTGAAGGTCATGGAC
CTGCCCACCCAGGAGCCAGCACTGGGGACCACCTGCTACGCCTCAGGCTGGGGCAGCATT
GAACCAGAGGAGTTCTTGACCCCAAAGAAACTTCAGTGTGTGGACCTCCATGTTATTTCC
AATGACGTGTGTGCGCAAGTTCACCCTCAGAAGGTGACCAAGTTCATGCTGTGTGCTGGA
CGCTGGACAGGGGGCAAAAGCACCTGCTCGGGTGATTCTGGGGGCCCACTTGTCTGTAAT
GGTGTGCTTCAAGGTATCACGTCATGGGGCAGTGAACCATGTGCCCTGCCCGAAGGCCT
TCCCTGTACACCAAGGTGGTGCATTACCGGAAGTGGATCAAGGACACCATCGTGGCCAAC
CCCTGA

FIG. 2

METHODS AND COMPOSITIONS RELATING TO A VACCINE AGAINST PROSTATE CANCER

CROSS-REFERENCE TO RELATED APPLICATION

This application claims priority based upon U.S. Provisional Application Ser. No. 60/692,238, filed 21 Jun. 2005.

TECHNICAL FIELD

The present invention relates generally to methods and compositions relating to a vaccines and, more particularly, to methods and compositions relating to a vaccine against prostate cancer.

BACKGROUND ART

Prior to a discussion of the background art, it is noted that the bracketed [ ] numbers in the discussion refer to the enumerated references in the Bibliographical References listed below at the end of the specification.

With respect to the background art, in the U.S.A., prostate cancer is the most frequently diagnosed form of cancer and the second leading cause of cancer death in males [2]. Current modalities of therapy for localized tumors include surgery and radiotherapy, and are generally successful. However, treatment for metastatic disease is not as beneficial, because current hormonal therapies work only transiently [3]. Therefore, new treatments for prostate cancer are needed.

Immunotherapy, based on CD8+ cytotoxic T lymphocytes (CTL) is one potential new avenue of therapy that holds much promise, especially for prevention and adjuvant treatment of metastatic disease [4,5]. CTLs recognize antigen in the form of a short peptide (8-10 amino acids) in a complex with class I major histocompatibility complex (MHC) on the surface of target cells. The ability of CTL to directly lyse these cells makes them attractive for tumor immunotherapy.

Prostate-specific antigen (PSA) has been proposed as a tumor antigen for the specific destruction of prostate carcinoma cells by CTLs. Tight tissue specificity of expression to the prostate, continued expression by prostate carcinoma cells, and the wealth of biochemical, genetic, and cell biological data available all make PSA an excellent candidate for characterization as potential target for prostate cancer immunotherapy.

Several PSA-based vaccines were evaluated in recently conducted clinical trials for stimulating an immune response against PSA in patients with advanced prostate cancer. These vaccines represented a recombinant vaccinia virus expressing PSA (rV-PSA) [6-9], a recombinant PSA protein formulated in liposomes [10], and autologous dendritic cells (DCs) pulsed with recombinant PSA protein [11] or transfected with PSA-encoding RNA [12].

CD8+ T Cells

The main biological function of CD8+ T cells is to eliminate pathogen-infected cells in the body. The mechanism responsible for T-cell recognition of infected cells is now well established at the molecular level and relies on interaction between a T-cell receptor complex (TCR) and an antigen-derived peptide bound to a major histocompatibility complex class I molecule (MHC I). All protein antigens produced by the cell are eventually degraded and the resulting peptides are presented by MHC I molecules on the cell surface.

Development of CD8+ T Cells

Development of T cells occurs in the thymus, where TCR α and β gene segments are rearranged such that each T cell clone eventually expresses a unique TCR [13]. Developing thymocytes that produce a surface TCR express CD4 and CD8 co-receptors and undergo a complex process of maturation, depending on the specificity and affinity of their TCRs for self-peptide MHC ligands. Thymocytes that express TCRs with no affinity for self-peptide-MHC molecules die by a programmed cell death mechanism. Potentially harmful thymocytes that express TCRs with strong affinity for the self-peptide-MHC ligands expressed on cells in the thymus are eliminated via physical deletion [14], functional inactivation [15], or receptor editing [16]. Only thymocytes that express TCRs with a low but significant affinity for self-peptide-MHC ligands on thymic stromal cells survive thymic selection [17].

Recirculation and Survival of Naive CD8+ T Cells

T cells that have not yet encountered a foreign peptide-MHC ligand for which their TCR has a high affinity are referred to as "naive" T cells. These cells account for the majority of T cells in the secondary lymphoid organs in healthy young adults. Naive T cells recirculate continuously through the secondary lymphoid organs, which include spleen, lymph nodes, and mucosal lymphoid organs (such as Peyer's patches of the intestines) [18, 19]. It is estimated that an individual naive T-cell will on average circulate through the secondary lymphoid organs for several months [20, 21]. Survival of naive CD8+ T cells during this normal lifespan is maintained by low-affinity TCR recognition of self-peptide-MHC complexes [22] and signaling through the IL-7 receptor [23, 24]. Although signals through the TCR and IL-7 receptor are required for the survival of naive T cells, these signals do not cause the T cells to proliferate in hosts containing normal numbers of T cells. In contrast, naive T cells proliferate when transferred into T-cell-deficient hosts. This "homeostatic" proliferation also depends on IL-7 [23, 24] and low-affinity TCR recognition of self-peptide-MHC complexes [25], but not IL-2 or the CD28 co-stimulatory receptor [26]. In young individuals, new naive T cells are constantly produced by the thymus and exported to the secondary lymphoid organs to replace senescent naive T cells. In contrast, in older individuals whose thymic output is reduced or absent, senescent cells may be replaced by proliferation of remaining naive T cells.

Activation of CD8+ T Cells

Naive CD8+ T cells migrating through the T-cell areas of secondary lymphoid organs encounter a dense network of large, irregular shaped dendritic cells (DCs) that constitutively express the highest levels of MHC molecules of any cell in the body (271. In the absence of infection or tissue damage, all DC populations in the secondary lymphoid organs exist in a resting state characterized by low expression of co-stimulatory molecules such as CD80 and CD86 [28]. In this state, DCs most likely play an important role in the presentation of low-affinity self-peptide-MHC ligands that maintains survival of naive T cells.

In the case of infection, various viral or bacterial products are recognized by pattern recognition receptors [29], for example, Toll-like receptors (TLRs) on cells of the innate immune system, including DCs. TLR signaling causes activation of DCs, which results in expression of higher levels of co-stimulatory molecules (CD80 and CD86) and production of inflammatory cytokines [30]. Activated DCs then function by presenting pathogen-derived peptide-MHC class I complexes to naive CD8+ T cells. In addition to a signal through TLR, naive CD8+ T cells also require additional signals through the co-stimulatory CD28 receptor and the IL-12 receptor to proliferate maximally and differentiate into cytotoxic effector cells [31-33]. All these signals can be provided to naive CD8+ T cells by activated DCs [34].

Naive CD8+ T cells show signs of DNA replication and cell division as early as 48 hours after exposure to antigen in vivo [35-37]. These events are followed by an exponential increase in the number of antigen-specific T cells over the next several days. Depending on the stimulus, the number of antigen-specific CD8+ T cells reaches its highest level in the secondary lymphoid organs, 7 to 15 days after activation with an antigen (FIG. 2,3) [35, 38-43].

In vitro experiments indicate that cell division by naive, antigen-stimulated T cells is driven by autocrine production of IL-2 [44]. Surprisingly, however, antigen-driven proliferation of naive T cells is minimally dependent on IL-2 in vivo [45-49]. Therefore, in addition to IL-2, other signals or growth factors must be also capable of driving T-cell proliferation in vivo.

In vivo T-cell proliferation is tightly regulated by co-stimulatory signals from DCs. The proliferation of antigen-stimulated CD8+ T cells is reduced dramatically in mice in which CD28 cannot interact with its ligands CD80 and CD86 [37, 45, 50]. CD40 ligand deficiency has a similar effect on T-cell expansion, which may be related to the fact that CD40 signaling induces CD80 and CD86 on antigen-presenting cells [51]. Co-stimulatory signals regulate T-cell proliferation by enhancing growth factor production. Antigen-driven IL-2 production is greatly impaired when CD28 signaling is eliminated [45].

Effector CD8+ T Cells

Antigen-specific CD8+ T cells at the peak of immune response express effector functions, and thus are sometimes referred to as "effector cells" [52]. Effector cells express a characteristic set of adhesion receptors. Unlike naive cells they express perforin and granzymes, which contribute to their defining feature, that is, the ability to directly kill target cells that display the appropriate peptide-MHC class I complexes. [53]. The effector T cells migrate out of the T-cell areas and into many nonlymphoid tissues, particularly inflamed sites of antigen deposition. The migration of effector CD8+ T cells with cytolytic potential into nonlymphoid organs is an effective way of eliminating cells that display peptide-MHC class I complexes from all parts of the body.

The number of effector T cells in the secondary lymphoid organs falls dramatically after the peak of proliferation [35, 38-43]. The molecular basis for death of effector T cells varies depending on the nature of the antigenic stimulus. In the case of a T cell response after a single administration of antigen, the death is Fas-independent and Bcl-2 sensitive [54] and occurs most likely due to deprivation of growth factors [55]. If antigen is presented chronically, TCR-mediated activation-induced cell death (AICD) may occur [56]. This type of apoptosis is dependent of Fas and is poorly inhibited by Bcl-2 [55].

IL-2 is playing a role in the AICD by preventing the activation of FLICE inhibitor protein, which normally inhibits Fas signaling [57]. The death of effector CD8+ T cells is regulated by inflammation. In the absence of inflammation, the loss of antigen-specific T cells from the secondary lymphoid and nonlymphoid organs after the peak of proliferation is nearly complete [58]. In contrast, many more cells survive the loss phase after injection of antigen together with adjuvants such as LPS or IL-1 [35, 58, 59].

Memory CD8+ T Cells

The vast majority of effector cells die after the peak of proliferation, nevertheless, a stable population of antigen-experienced T cells survive for long periods of time if the antigen was initially presented in an inflammatory context [52]. In many ways, memory cells can be thought of as effector cells that have returned to a basal activation state. Indeed, several lines of evidence suggest that effector cells are precursors of memory cells [60, 61].

Unlike naive CD8+ T cells, memory CD8+ T cells do not depend on MHC-class 1 molecules for survival [62]. Whereas most memory CD8+ T cells are not cycling, a small fraction of the memory population is proliferating in an MHC class I-independent fashion at all times [47, 62]. This proliferation is balanced by death since the total number of antigen-specific memory CD8+ T cells remains unchanged over time. Several observations suggest that IL-15 plays a role in this process. The antigen-independent proliferation of memory CD8+ T cells is accelerated by injection of IL-15 [63] and blocked by injection of antibodies against IL-15 [47]. In addition, memory CD8+ T cells are diminished in IL-15-deficient mice [64]. Since IL-15 is produced by non-T cells during the innate immune response, it is possible that memory CD8+ T cells are maintained as a consequence of IL-15 produced in response to other infections [63, 65].

Prostate-Specific Antigen (PSA)

Prostate-specific antigen (PSA) is a kallikrein-like, serine protease that is produced exclusively by the columnar epithelial cells lining the acini and ducts of the prostate gland [66-68]. PSA is secreted into the lumina of the prostatic ducts and is present in the seminal plasma at rather high concentrations ranging from approximately 0.5 to 5 mg/ml [69]. Physiologically, PSA functions in seminal plasma to cleave the major gel-forming proteins semenogelin I and II, and fibronectin, resulting in increased sperm motility [67, 70, 71]. PSA is translated as an inactive 261 amino acid preproPSA precursor. PreproPSA has 24 additional residues that constitute the pre-region (the signal peptide) and the propeptide. Release of the propeptide results in the 237-amino acid, mature extracellular form, which is enzymatically active. Human glandular kallikrein 2 (hKLK2), which like PSA is preferentially expressed in the prostate tissue, is responsible for the activation of proPSA [72]. PSA has been shown to contain an N-linked oligosaccharide attached to asparagine-69 [73].

PSA is also released into the blood at low concentrations. In healthy males without clinical evidence of prostate cancer, the concentration of PSA detected in the serum is usually less than 4 ng/ml [74-76]. Enzymatically active PSA is inactivated in the blood by forming covalently linked complexes with $\alpha_1$-antichymotrypsin (ACT) [77, 78]. Enzymatically inactive (internally clipped) PSA is incapable of forming complexes with protease inhibitors and circulates as a free, uncomplexed form in the blood [79].

PSA is organ-specific and, as a result, it is produced by the epithelial cells of benign prostatic hyperplastic (BPH) tissue, primary prostate cancer tissue, and metastatic prostate cancer tissue [66, 80]. Normal prostate epithelial cells and BPH tissue actually produce more PSA protein than malignant prostate tissue [81, 82]. Therefore, PSA is not a traditional tumor marker that is produced in higher quantities by tumor cells, but rather abnormalities in the prostate gland architecture resulting from trauma or disease can lead to increased "leakage" of the enzyme into the stroma and then into the bloodstream via capillaries and lymphatics.

The most common use of PSA in the clinic is for monitoring prostatic cancer therapy. If a patient undergoes a radical prostatectomy, serum PSA levels should decrease to undetectable concentrations because all of the source tissue has been removed [83, 84]. Increasing PSA concentrations after surgery, indicate a recurrence of the disease [83, 85, 86]. PSA also reflects the success of radiotherapy and anti-androgen (hormonal) therapy in prostate cancer patients [87-89].

Plasmid DNA Vaccines Against Cancer

In recent years a number of tumor vaccination strategies have been developed. Most of them rely on identification of tumor antigens that can be recognized by the immune system. DNA vaccination represents one such approach for the induction of both humoral and cellular immune responses against tumor antigens. Studies in animal models demonstrated the feasibility of using DNA vaccination for eliciting protective anti-tumor immune responses. However, most tumor antigens expressed by cancer cells in humans are weakly immunogenic, which requires development of strategies to potentiate DNA vaccine efficacy in the clinical setting. Recent advances in understanding the immunology of DNA vaccines and strategies used to increase DNA vaccine potency with respect to CTL activity are discussed below.

Immunology of DNA Vaccines

A DNA vaccine usually represents a simple plasmid DNA expression vector. It contains cDNA encoding a desired antigen inserted between a eukaryotic promotor and a polyadenylation sequence, bacterial antibiotic resistance gene and a bacterial origin of replication. The eukaryotic promotor and polyadenylation sequence are required for proper antigen expression in mammalian cells, and the antibiotic resistance gene and origin of replication allow production of the vector in bacteria.

After administration of the naked plasmid DNA by intramuscular (i.m.) or intradermal (i.d.) inoculation, host cells take up the DNA and produce the encoded antigen, which then serves as a target for the immune response [90-93]. The expression of the antigen in vivo is commonly achieved by using strong viral promoters, which are ubiquitously active and will drive antigen production in a wide range of cell types. The human cytomegalovirus immediate early enhancer-promotor (known as the CMV promotor) is often the promotor of choice [94]. DNA vaccination results in generation of adaptive immune responses comprising of regulatory components such as: induction of antigen-specific CD4+ helper T cells; and effector components such as: production of antibodies recognizing native antigen, and effector CD8+ cytotoxic T lymphocytes (CTLs). The latter are directed against antigen-derived peptides presented by class I major histocompatibility molecules (MHC class I) on the cell surface.

The potential of DNA encoding a protein antigen to generate CTL responses has attracted a lot of attention, since immunization with purified recombinant proteins does not efficiently induce CTLs (reviewed in [95, 96]). Studies in mice of the underlying mechanism revealed that induction of helper CD4+ T cells and direct activation of antigen-presenting cells (APCs) by DNA molecules contributes to the successful CTL priming by DNA vaccines. The latter requirement was suggested to be somewhat redundant (see below).

Here we summarize the key findings, which are starting to elucidate the observed immunogenicity of DNA vaccines.

The CD8+ T-cell response after DNA vaccination was shown to be initiated by bone marrow-derived APCs, such as dendritic cells (DCs) [97-99]. The relevant APCs can be directly transfected with plasmid DNA, which then leads to antigen production within the cell, or they may pick up antigen expressed and released by other cells (the latter mechanism is referred to as cross-presentation/cross-priming) [100-102]. In both cases, the antigen is processed by proteolytic digestion inside the APCs and the resulting peptides are presented by MHC class 1 molecules on the cell surface for priming of naive CD8+ T cells. Which of these two mechanisms is the predominant one in vivo is still a matter of a debate and may vary among different DNA administration methods [102-104].

Nevertheless, certain modifications of the antigens (including linkage with ubiquitin [105] or heat shock proteins [106, 107]) may improve their targeting to the conventional or cross-priming MHC class I presentation pathway (reviewed in [108]).

The backbone of plasmid DNA was shown to contain immunostimulatory nucleotide sequences, which are composed of unmethylated CpG dinucleotides, with particular flanking nucleotides (referred to as CpG motifs) [109-111]. Due to differences in frequency of utilization and methylation pattern of CpG dinucleotides in eukaryotes versus prokaryotes, such sequences are approximately 20 times more common in bacterial then in mammalian DNA [112, 113]. The CpG motifs were shown to act through Toll-like receptor 9 (TLR9) [114], which is expressed in mice on macrophages, DCs and B cells, but in humans only on plasmacytoid DCs and B cells [115-117]. The direct interaction of TLR9 and CpG-containing plasmid DNA was shown to result in upregulation of co-stimulatory molecules on APCs and induction of the proinflammatory cytokines IL-12, IL-6, IL-18, TNFα, IFNα/β and IFNγ, secreted by various cells of innate immune system [118-121].

Activation of APCs is known to be important for efficient priming of naive CD8+ T cells and thus presence of certain CpG motifs in the backbone of DNA vaccines was suggested to contribute to CTL induction [122]. Surprisingly, repeated DNA immunization of mice with deficiency in the TLR9 signaling pathway (TLR9−/− or MyD88−/− mice) results in development of normal CTL responses, similar to those in wild-type mice, despite the fact that no direct stimulation of APCs by plasmid DNA could be observed in these mice [123, 124]. This finding suggests that activation of APCs by CpG-motifs might be redundant in the context of DNA vaccines, and necessary activation of APCs in vivo can possibly occur indirectly, through induction of helper CD4+. T cells (reviewed in [125]). In fact, DNA immunization experiments in mice either depleted of CD4+ T cells or having deficiency in CD4+ T cell compartment (CD4−/− or MHC class II−/− knockouts) demonstrated that the presence of CD4+ T cells is a critical requirement for generation of effector CTL responses [126-128].

DNA Vaccines Against Cancer in Animal Models

The utility of DNA vaccines in developing protective anti-tumor responses was first demonstrated with model tumor antigens in mice. DNA immunization with plasmids encoding the SV40 large T-antigen [146], β-galactosidase [147], human carcinoembryonic antigen (CEA) [148], human papillomavirus E7 [149] or human PSA [150] were shown to protect mice from lethal challenge with syngeneic tumor cells expressing the corresponding antigen. Depletion studies provided evidence for the role of CD8+ cytotoxic T lymphocytes in the tumor rejection [147, 149]. Altogether these studies demonstrate the feasibility of using DNA vaccines for inducing antigen-specific immune responses targeting tumor cells. However, all of the antigens used in these studies were in fact foreign proteins which typically are much more immunogenic than the "regular" tumor antigens which represent self-antigens.

Several murine models were established to allow testing of DNA vaccine potency against tumor antigens that more closely resemble those that would be encountered clinically. These approaches rely on the use of transgenic mice expressing model tumor antigens in a tissue specific manner [151, 152], or testing DNA vaccines that target the murine counterparts of human tumor antigens [153, 154].

DNA immunization against the P815A antigen, a murine equivalent of human tumor-specific antigens belonging to the MAGE family [155], was shown to induce CTLs and protect mice from lethal tumor challenge [153]. This finding suggested that the T cells could be readily induced against natural tumor-specific antigens, which are silent in most normal tissues.

In contrast, naturally occurring tumor-associated antigens were shown to have low intrinsic immunogenicity. While a DNA vaccine encoding human proto-oncogene Her2 readily induced an antibody response in wild-type mice, the same vaccine induced only a modest antibody response in Her2 transgenic mice and provided weak tumor protection [152]. Similar results were also obtained for CTL responses in Her2/neu transgenic mice. Immunization with the rat neu DNA vaccine induced protective CTL responses in wild-type mice, but was not effective in transgenic animals where no CTL response was observed [156]. The ability of the rat neu DNA vaccine to induce CTL responses in wild-type mice could probably be explained by the differences in the amino acid sequence between the neu-derived CTL epitope and the corresponding sequence of the murine Her2 counterpart (c-erbB-2) [156, 157]. Thus, CD8+ T cells capable of recognizing the neu-derived epitope are present in wild-type mice, but are most likely deleted during thymic selection or anergized in the periphery in neu-transgenic animals.

In line with these findings, DNA immunization against murine melanocyte differentiation antigens TRP-1, TRP-2 (tyrosinase-related proteins), and gp100 were also unsuccessful [154, 158, 159]. Interestingly, the same studies demonstrated that immunization of mice with the xenogeneic (human) DNA encoding TRP-1, TRP-2, or gp100 resulted in induction of immune responses and protection from syngeneic tumor challenge with B16 mouse melanoma cells. The anti-tumor immunity was mediated by antibodies upon vaccination with human TRP-1, and by CD8+ T cells in the case of human TRP-2 and gp100 (reviewed in [160]) A significant conclusion of these observations is that immunization with syngeneic (mouse) genes does not induce T-cell or antibody responses, while immunization with xenogeneic (human) genes can lead to the generation of antibodies and CTLs capable of recognizing both the human and mouse proteins. For CTL responses, the mechanism underlying such cross-reactivity was shown, in case of gp100, to represent the random creation of a heteroclitic epitope in the human sequence with better binding capacity to a MHC class I antigen [161]. Thus, a DNA vaccine encoding human gp100 induces CD8+ T cells that are directed against this "human" epitope and are also capable of recognizing the corresponding murine endogenous sequence ("murine" epitope) [159, 162]. For cross-reactive antibody responses, the presence of strong helper epitopes within the xenogeneic sequence was suggested [163]. To this end, research on DNA vaccines in animal models have shown some promising results regarding tumor protection. Challenges remain, however, for the use of DNA vaccines as a therapeutic tool, which is more reflecting the clinical setting. Further understanding of the mechanisms underlying the formation of the T cell repertoire during T cell maturation in the thymus and exact mapping of epitope specificity for "self" tumor antigen reactive CTLs, should provide further help for the rational design of DNA vaccines capable of inducing more potent immune responses particularly against tumor-associated antigens.

Enhancing Potency of DNA Vaccines

Studies in mice have demonstrated that the frequencies of antigen-specific CTLs induced by DNA vaccines are around 10-fold lower when compared to virally induced responses, and the primary effector CTL response after a single DNA immunization is slightly delayed, peaking at 12-15 days after immunization [164, 165]. These qualitative differences in primary CTL responses could be in part attributed to the minute amounts of antigen produced after plasmid DNA administration [90] and inefficient targeting of APCs in vivo, which altogether is not sufficient to ensure robust priming and expansion of naive T cells.

Several approaches for DNA delivery have been developed which provide elevated amounts of antigen produced and/or improved targeting of APCs in vivo, when compared to the commonly used i.m. or i.d. injection of DNA in saline. These techniques include biolistic inoculation of DNA-coated gold particles into the skin, targeting resident antigen presenting Langerhans cells (also referred to as "gene-gun" technique) [91, 102], the use of cationic poly(DL-lactide-co-glycolide) (PLG) microparticles with DNA adsorbed onto the surface [166, 167], or application of pulsed electrical fields (also referred to as electroporation in vivo) at the injection site either after i.m. or i.d. DNA administrations [168-171]. It is worthwhile to note here that direct injection of naked DNA into a peripheral lymph node was shown to induce strong CTL responses, which were qualitatively and quantitatively superior to that achieved by conventional i.m. or i.d. inoculation routes [172]. This finding suggests that efficacy of priming of naive T cells after DNA immunization correlates with the strength and duration of antigenic stimulus in secondary lymphoid organs.

The immunogenicity of DNA vaccines can also be enhanced by various modifications of the plasmid-encoded antigens. Codon optimization of the encoding DNA sequences has been shown to increase antigen expression resulting in superior antibody and CTL responses after DNA vaccination [173, 174]. Linking of the antigen to a ubiquitin monomer [105] or heat shock proteins [106, 175] enhanced antigen-specific CTL responses, presumably via improved targeting of these fusion proteins to the conventional or cross-priming MHC class I presentation pathways.

Another strategy to optimize induction of immune responses by DNA vaccines is based on the fact that induction of helper CD4+ T cells significantly contributes to the generation of effector CTL and antibody responses (see section 4.1). Providing CD4+ T cell help by means of linkage of a tumor antigen with a microbial or viral antigen, containing strong helper epitopes, was shown to result in enhanced antibody and CTL responses against the tumor antigen after DNA vaccination (reviewed in [176]).

It is important to mention that design of such tumor antigen—"helper" antigen fusion constructs, with the aim to enhance tumor antigen-specific CTL responses, requires an additional consideration. A naturally occurring focusing of CTL responses onto a very few peptide epitopes from a large antigen, known as the phenomenon of immunodominance, is observed also with DNA vaccines [177, 178]. Thus, in order to ensure that the CTL response develops against tumor antigen-derived epitopes rather than "helper" antigen-derived ones, all potential CTL epitopes in the "helper" portion of the fusion should be removed. [179, 180].

Although, recent experiments in TLR9−/− and MyD88−/− mice have demonstrated that activation of APCs by the plasmid DNA backbone is not absolutely required for induction of immune responses [123, 124], the CpG-mediated stimulation of APCs could provide certain adjuvant effects for DNA vaccines. The CpG motifs provided in the form of synthetic oligodeoxynucleotides (CpG-ODNs) were shown to act as adjuvants promoting better antibody and CTL responses after DNA vaccination (reviewed in [181]). The adjuvant effect of CpG-ODNs is very profound in combination with low DNA vaccine doses, but only modest with higher doses of DNA vaccine [182]. It is important to emphasize, that the CpG-ODNs providing optimal immunostimulatory activity in mice differ in sequence from those functioning in primates [183].

Several other strategies for enhancing the potency of DNA vaccines have focused on the use of various immunostimulatory molecules including cytokines and costimulatory molecules (reviewed in [184, 185]). These adjuvants can be administered in the form of recombinant proteins or as a separate plasmid encoding the selected molecule. The rationale behind such approaches is commonly based on facilitating priming of T cells by providing additional signals through cytokine/costimulatory molecules, which otherwise might not be optimal when using plasmid DNA vaccines alone. Examples of successful application of this approach include enhanced antibody and CTL responses leading to better protection against tumor challenge in mice immunized with CEA-encoding plasmid together with IL-12 expressing plasmid [186], and enhanced antibody/CTL responses after co-administration of an antigen-encoding DNA vaccine and plasmid expressing murine granulocyte-macrophage colony-stimulating factor (GM-CSF) [187], [188].

While all of the above-mentioned strategies were generally shown to increase immunogenicity of DNA vaccines encoding model antigens, no selected strategy is yet firmly established to provide better priming of CTL or antibody responses after DNA immunization against poorly immunogenic "self" tumor antigens in appropriate murine models and more importantly in clinical settings.

DNA Vaccines Against Cancer in Clinical Trials

Here we discuss several recently conducted Phase I clinical trials on DNA vaccination targeting tumor-associated antigens in patients with HPV-associated anal dysplasia [213], metastatic colorectal carcinoma [212], B-cell lymphoma [214], metastatic melanoma [215, 216] and prostate cancer [211, 217]. A number of different DNA delivery techniques and adjuvants were employed in these studies, which well represent current advances within the DNA vaccination field.

A standard dose escalation scheme was followed in most of these trials, with no DNA vaccine dose escalation in individual patients. DNA vaccination was applied as monotherapy and the patients had not undergone any other form of therapy within at least 3 weeks prior to entering trials, except for the studies in prostate cancer, where patients were concurrently receiving a hormonal therapy [217].

Due to the limited numbers of patients enrolled in these trials, the main objectives in all of the studies were to evaluate the safety of plasmid DNA administration, to monitor immune responses induced by the vaccines in a dose-dependent manner, and to assess correlation between vaccine-induced immune responses and the clinical benefits.

Collectively, these trials have shown that repetitive DNA administrations were well tolerated with no dose-limiting toxicities observed even with DNA doses reaching up to 2 mg per injection [212], demonstrating that repetitive immunizations with DNA is a safe procedure.

With regard to induction of immune responses, the "foreign" antigens were shown to be more immunogenic than the "self" tumor-associated antigens. Immunization with DNA vaccine encoding human papillomavirus E7-derived CTL epitope(s) induced T cell responses detected by IFNγ ELISPOT assay in 10 of 12 subjects [213]. A dual expression plasmid encoding CEA and hepatitis B surface antigen (HbsAg—included in the study as a control "foreign" antigen) induced HbsAg-specific antibody responses in 6 of 8 patients that were immunized repeatedly [212]. Lymphoproliferative or antibody responses against murine immunoglobulin (Ig) constant regions were also observed in 8 of 12 patients vaccinated with plasmid DNA encoding chimeric Ig molecules [214]. In contrast the rates of immune responses against autologous tumor-associated antigens were relatively low. In above-mentioned studies, CEA-specific antibody responses were not observed and only 4 of 17 patients developed lymphoproliferative responses to CEA, which showed no clear relationship to the dose or schedule of plasmid DNA immunization [212]. Similarly, only 1 of 12 patients immunized with chimeric Ig molecules developed a transient T cell response against autologous tumor-derived idiotypic (Id) determinant [214]. No CTL responses were detected against gp100-derived HLA-A2 restricted CTL epitopes in melanoma patients that were immunized with DNA encoding modified gp100 antigen [215], despite the fact that a recombinant fowl poxvirus encoding the same DNA construct was shown to induce CTL activity in 4 of 14 patients in previously performed study [218]. Transient CTL responses against a novel tyrosinase-derived HLA-A2 restricted epitope were observed overall in 11 of 24 melanoma patients, which received plasmid DNA encoding this epitope by infusions into a lymph node [216].

In the study combining repetitive administrations of a DNA vaccine and a recombinant adenovirus expressing PSMA, all patients eventually developed positive DTH response to a PSMA plasmid DNA injection, suggesting an induction of cellular immune response against PSMA, but these results were not further confirmed by other conventional in vitro assays [217].

In our recent clinical trial of DNA vaccination in patients with hormone-refractory prostate cancer, PSA-specific T cell immune responses were observed in 2 of 9 patients, with both responders being in the cohort receiving the highest DNA dose tested. [211]. A trend towards dose-dependent induction of T cell immune responses against tumor-associated antigens were observed in several of these studies [211, 214], although the epitope specificities of the reactive T cells have yet to be determined in order to firmly demonstrate presence of CTLs.

Clinical benefits of DNA vaccination as monotherapy were only modest and included: one patient with B-cell lymphoma experienced the tumor regression in bone marrow [214], three subjects with high-grade anogenital dysplasia achieved a partial histological response [213], two patients with prostate cancer exhibited stabilization of disease as judged by a decrease in serum PSA levels [211] and superior survival of the eleven melanoma patients who had detectable immune responses against tyrosinase compared with the thirteen patients who had no immune response [216]. The correlation of clinical benefits with vaccine induced-immune responses was observed only in the two latter studies [211, 216].

In summary, repetitive DNA vaccinations have shown a good safety profile in clinical settings even at high DNA doses (at 1 mg range), which seem to be required for induction of T cell immune responses in humans. The low frequency of responses may have resulted in part from the compromised immune status of the advanced stage patients enrolled in these trials. Future clinical trials can focus on patients during a remission phase or with minimal residual disease, where more pronounced clinical benefits of DNA vaccines are more likely to occur.

Xenogeneic Vaccines

It is naturally easier to induce an immune response to a foreign antigen than it is to a self antigen. For that reason, it is helpful to make an antigen as foreign as possible and still induce an immunity to the self protein. One strategy for doing this is to attach a foreign protein to a native self protein. A commonly used protein for this is keyhole lymphet cyanogen. Induction of an immune response to KLH often induces an immune response to the attached protein.

Another strategy is to use proteins similar to the native self protein but taken from another species of animals. This is called a xenogeneic protein. This has been done with a prostate antigen called prostate specific membrane antigen (PSMA). Wolchok et al used human PSMA in mice and induced a good immune response in mice to the mouse PSMA. There is currently a clinical trial using rodent xenogeneic PSMA in humans.

The strategy of using xenogeneic protein has been used in other species. Human tyrosinase was used to immunize dogs with melanoma. In general, the species have been chosen with wide differences between the species.

Publications describe the use of xenogeneic or xenogeneic antigens to induce an immune response. This includes the accidental but unrecognized use of xenoantigens such as when human PSA is used in mice. It also includes the deliberate use of xenoantigens. An example of the deliberate use of xenoantigens is the immunization of dogs with human antigens for vaccines against melanoma (Bergman et al, 2003, Long-term survival of dogs with advanced malignant melanoma after DNA vaccination with xenogeneic human tyrosinase: a phase 1 trial, Clinical Cancer Research, 9:1284-1290). The publications do not describe the use of xenogeneic proteins with minimal interspecies differences between the xenogeneic protein and the native protein to induce an optimal immune response to the native self antigen.

The human protein PSA was discovered and characterized in the 1970's. The PSA protein was first purified in 1979. Anti-rabbit serum was prepared from the protein and tissues analyzed. The human PSA was only found in prostatic tissues and not other tissues. Wang et al Purification of a human prostate specific antigen 1979, Invest. Urol. 17:159-63. Others have found human PSA in smaller amounts in other tissues. It is expressed at low levels in other epithelial like cells in lung and breast tumors. Zarghami et al Frequency of expression of prostate-specific antigen mRNA in lung tumors, 1997 μm J Clin Pathol 108(2): 184-90. Smith et al Prostate-specific antigen messenger RNA is expressed in non-prostate cells: implications for detection of micrometastases 1995 Cancer Res. 55(12): 2640-44.

The gene for human prostate-specific antigen was sequenced in 1989. Digby et al Human prostate specific antigen (PSA) gene: structure and linkage to kallifrein-like gene 1989 Nucleic Acids Research, 17(5): 2137. Klobeck et al, Genome sequence of human prostate specific antigen, 1989 nucleic Acids Research 17(10):3981

The cDNA sequence of Homo Sapiens PSA is recorded in Genebank. One sequence is listed in Genebank Accession Number AJ459783. Another was published in 1988 and submitted as Genebank Accession Number X07730 (Schultz et al. Sequence of a cDNA clone encompassing the complete mature human Prostate Specific Antigen (PSA) and an unspliced leader sequence. 1988 Nucleic Acids Research 16(13):6226. Still another human cDNA human sequence is listed as Genebank Accession Number BC056665.

The cDNA sequence of the non-human primate Cynomolgus monkey (Macaca fasicularis) prostate specific antigen precursor cDNA is published as Genebank Accession Number AY647976.

In addition, the cDNA sequence of the Rhesus monkey (Macaca mulatta) prostate specific antigen is published as Genebank Accession Number X73560.

A comparison of the preceding three genes shows that there are 30 base pair differences between human PSA and either rhesus or Cynolomogus PSA cDNA. This is a 3.8% difference. The resulting amino acid difference is 9.9% for the rhesus monkey PSA compared to human PSA and 10.7% for the Cynamologus monkey PSA compared to human.

The attached three page DNA Sequence Comparison (in FIGS. 1A, 1B, and 1C) shows the homology among the cDNA gene sequence for human PSA (cDNA on Genebank Accession # BC056665), the cDNA gene sequence for Maccaca mulatto PSA, and the cDNA gene sequence for Macca fascicula PSA.

Aside from the scientific literature discussed above, a review of published and issued patents reveal the following relevant patents and published patent application.

United States Published Application 20040141958 discloses novel methods for therapeutic vaccination and discusses the use of self peptides or proteins with foreign peptides representing CTL epitopes. This would be a chimeric protein. It does not address the use of entire foreign proteins to induce a cross reactive immunity to native proteins.

U.S. Pat. No. 5,925,362 discloses a method to elicit an antitumor response with human prostate specific antigen. This patent describes a prostate cancer vaccine requiring two parts. One is human PSA and the other is an expression system for producing the human PSA in situ. This is a DNA vaccine expressing human PSA. It does not describe the use of a xenogeneic PSA DNA vaccine.

U.S. Pat. No. 6,165,460 discloses the generation of immune responses to human prostate specific antigen (PSA). This patent describes a PSA DNA vaccine. One claim describes a pox virus vector used for expressing PSA. It does not specifically state human PSA but xenogeneic PSA is not mentioned. Another claim teaches the use of PSA (or PSA CTL epitope) followed by a second administration of additional PSA. This is a traditional vaccine boost strategy that includes boosting with a different PSA expressing vector or with PSA protein itself. A third claim mentions the use of a CTL eptipoe only. Although the animal model used to evaluate the vaccine was a rhesus monkey model using human PSA, there was no mention of the opposite approach of using of rhesus monkey PSA in humans.

U.S. Pat. Nos. 6,818,751; 6,800,746; 6,759,515; 6,664,377; 6,657,056; 6,630,305; 6,620,922; 6,613,872; 6,329,505; 6,262,245; 6,261,562; 5,854,206 all describe the use of prostate specific peptides for diagnosis of prostate cancer, generation of monoclonal antibodies against the peptides, and immunotherapy of prostate cancer. They do not discuss the use of xenogeneic PSA as an immunogen.

U.S. Pat. No. 6,699,483 discloses cancer treatments which employ the use of three human prostate cancer cell lines in a prostate cancer vaccine. The cell lines are human and represent a broad range of antigens. It does not describe the use of xenogeneic cell lines, xenogeneic PSA or the use of DNA vaccines.

From the above discussion, a wide variety of approaches have been discussed in the scientific literature relating to vaccines, including xenogeneic approaches.

For purposes of the present invention, a brief review of relevant points is provided.

It is known that when a non-human antigen is introduced into a human, a human immune response produces antibodies against the non-human antigen.

It is believed that, in certain limited specific cases, when a specific-case non-human antigen is introduced into a human, a human immune response produces antibodies against a similar specific-case human antigen.

Only primates have prostate specific antigen (PSA). Humans have human-PSA, and non-human primates have non-human-primate-PSA. Species such as mice and dogs have serine proteases that are kallikrien proteins, but they are different enough from PSA so they are not considered to be PSA.

Non-human primates include the rhesus monkey and the chimpanzee, among others.

Human-PSA is comprised of a sequence of approximately 260 amino acids (See FIG. 2, section "huPSA"). Rhesusy-monkey-PSA is comprised of a sequence of approximately 260 amino acids (See FIG. 2, section "rhPSA"). Approximately 10% of the amino acids in the rhesus-monkey-PSA amino acid sequence differ from the amino acids in the human-PSA amino acid sequence.

Though there are similarities between human-PSA and xenogeneic-PSA, such as Rhesus-monkey-PSA, the differences between the human-PSA and the Rhesus-monkey-PSA are so significant that laboratory tests for detection of human-PSA will not detect xenogeneic-PSA such as Rhesus-monkey-PSA.

Turning specifically to prostate cancer in humans, treatment of human prostate cancer involves surgically removing the entire prostate gland. Further treatment of prostate cancer involves trying to destroy prostate cells that escaped surgical removal. In this respect, an anti-prostate vaccine should be designed to kill all prostate cells that escaped surgical removal.

Human prostate cells produce human-PSA, and a vaccine against human prostate cancer should cause triggering a human immune response that brings about the killing of human cells that produce human-PSA. In this way, prostate cells that escaped surgery would be killed as a result of vaccination with the vaccine against human prostate cancer.

In view of the prior art, it is an insight of the present inventors, resulting in the present invention, that it would be desirable to use a xenogeneic antigen (e.g. protein) in a human, wherein, with respect to the xenogeneic antigen that is used, there are relatively few interspecies differences between the xenogeneic antigen and the human self antigen in order to induce an optimal immune response in the human to its native self antigen.

Another insight of the present inventors, resulting in the present invention, is that it would be desirable to use a non-human primate xenogeneic antigen (e.g. protein) in a human, wherein, with respect to the non-human primate xenogeneic antigen that is used, there are relatively few interspecies differences between the non-human primate xenogeneic antigen and the human self antigen in order to induce an optimal immune response in the human to its native self antigen.

A more specific insight of the present inventors, resulting in the present invention, is that it would be desirable to use a non-human primate xenogeneic PSA antigen in a human, wherein, with respect to the non-human primate xenogeneic PSA antigen that is used, there are relatively few interspecies differences between the non-human primate xenogeneic PSA antigen and the human self PSA antigen in order to induce an optimal immune response in the human to its native self PSA antigen.

An even more specific insight of the present inventors, resulting in the present invention, is that it would be desirable to provide a method for inducing an immune response against human PSA in humans using a non-human PSA having an amino acid homology $\geq 88\%$ and $\leq 98\%$ (or a 2 to 12% difference) with respect to the human PSA.

More specifically, the subject method includes obtaining PSA isolated from non-human primates and molecularly altering the non-human-primate PSA to adjust the amino acid homology to an optimal homology balance with respect to the human PSA. More specifically, it is desirable to provide an optimal homology balance such that the amino acid sequence in the non-human-primate PSA has a homology that is different enough from the amino acid sequence of the human PSA to induce an immune response to the non-human-primate PSA in the human but similar enough to produce an immune response in the human to human PSA.

The present invention also includes a DNA sequence whereby expression of that sequence produces a protein with an amino acid sequence with 88 to 98% homology to human PSA. It also includes the use of the DNA sequence in a polynucleotide vaccine such as a DNA or RNA vaccine.

A rationale for using non-human primate PSA rather than artificially made PSA is that all of the changes in the natural selection of a protein that maintains serine protease activity selects proteins with similar conformation. This means that immune responses to areas of the protein that are conformationally dependent are more likely to be similar or the same among the human and primate xenogeneic PSA.

In accordance with the present invention, delivery of the vaccine can be by a variety of methods including injection with or without chemical enhancers of transfection, biolistic methods, or electroporation for example.

Thus, while the foregoing body of prior art indicates it to be well known to use xenogeneic antigens for eliciting some immune responses in non-human animal models, the prior art described above does not teach or suggest methods and compositions relating to a vaccine against prostate cancer which has the following combination of desirable features: (1) an anti-prostate vaccine which is designed to kill prostate cells that have escaped surgical removal; (2) causes a triggering of a human immune response that brings about the killing of human cells that produce human-PSA; (3) is not limited to hormonal therapies; (4) uses a xenogeneic antigen (e.g. protein) in a human, wherein, with respect to the xenogeneic antigen that is used, there are relatively few interspecies differences between the xenogeneic antigen and the human self antigen in order to induce an optimal immune response in the human to its native self antigen; (5) uses a non-human primate xenogeneic antigen (e.g. protein) in a human, wherein, with respect to the non-human primate xenogeneic antigen that is used, there are relatively few interspecies differences between the non-human primate xenogeneic antigen and the human self antigen in order to induce an optimal immune response in the human to its native self antigen; and (6) uses a non-human-primate xenogeneic PSA antigen in a human, wherein, with respect to the non-human-primate xenogeneic PSA antigen that is used, there are relatively few interspecies differences between the non-human-primate xenogeneic PSA antigen and the human self PSA antigen in order to induce an optimal immune response in the human to its native self PSA antigen. The foregoing desired characteristics are provided by the unique methods and compositions relating to a vaccine against prostate cancer of the present invention as will be made apparent from the following description thereof. Other advantages of the present invention over the prior art also will be rendered evident.

DISCLOSURE OF INVENTION

An object of the present invention is to provide new and improved methods and compositions relating to a vaccine against prostate cancer which is designed to kill all prostate cells that escaped surgical removal.

Still another object of the present invention is to provide new and improved methods and compositions relating to a vaccine against prostate cancer that causes a triggering of a human immune response that brings about the killing of human cells that produce human-PSA.

Yet another object of the present invention is to provide new and improved methods and compositions relating to a vaccine against prostate cancer which is not limited to hormonal therapies.

Even another object of the present invention is to provide new and improved methods and compositions relating to a vaccine against prostate cancer that uses a xenogeneic antigen (e.g. protein) in a human, wherein, with respect to the xenogeneic antigen that is used, there are relatively few interspecies differences between the xenogeneic antigen and the human self antigen in order to induce an optimal immune response in the human to its native self antigen.

Still a further object of the present invention is to provide new and improved methods and compositions relating to a vaccine against prostate cancer which uses a non-human primate xenogeneic antigen (e.g. protein) in a human, wherein, with respect to the non-human primate xenogeneic antigen that is used, there are relatively few interspecies differences between the non-human primate xenogeneic antigen and the human self antigen in order to induce an optimal immune response in the human to its native self antigen.

Yet another object of the present invention is to provide new and improved methods and compositions relating to a vaccine against prostate cancer that uses a non-human-primate xenogeneic PSA antigen in a human, wherein, with respect to the non-human-primate xenogeneic PSA antigen that is used, there are relatively few interspecies differences between the non-human-primate xenogeneic PSA antigen and the human self PSA antigen in order to induce an optimal immune response in the human to its native self PSA antigen.

In accordance with one aspect of the invention, a composition of matter is provided which includes non-human-primate-PSA and a pharmaceutically acceptable carrier for administration to humans.

In accordance with another aspect of the invention, a vaccine is provided for humans which is comprised of non-human-primate-PSA and a pharmaceutically acceptable carrier for administration to humans.

In accordance with another aspect of the invention, a vaccine is provided wherein the non-human-primate-PSA triggers a human immune response which produces antibodies against human-PSA.

In accordance with another aspect of the invention, the use of non-human-primate PSA is provided for the preparation of a vaccine for administration to humans to provide an immune response against human PSA.

In accordance with another aspect of the invention, a vaccine is provided wherein a human immune response results in cytotoxic, cell-mediated immunity against human cells which contain human-PSA.

In accordance with another aspect of the invention, a method of treating humans includes steps for introducing a non-human-primate-DNA sequence into a human for providing non-human-primate-PSA in the human.

In accordance with another aspect of the invention, the use of a non-human-primate DNA sequence is provided for providing an antigen, for the preparation of a vaccine for administration to humans to provide an immune response to the antigen in humans. In accordance with another aspect of the invention, the use of a non-human-primate DNA sequence for PSA is provided for the preparation of a vaccine for administration to humans to provide an immune response against human PSA.

In accordance with another aspect of the invention, a method of treating prostate cancer in humans is provided which includes the step of introducing non-human-primate-PSA into a human for triggering a human immune response which produces antibodies against human-PSA.

In accordance with another aspect of the invention, a method of treating prostate cancer in humans is provided which includes the step of introducing non-human-primate-PSA into a human, wherein a human immune response results in production of antibodies against human-PSA.

In accordance with another aspect of the invention, a method of treating prostate cancer in humans is provided which includes the step of introducing non-human-primate-PSA into a human for triggering an immune response which includes cytotoxic, cell-mediated immunity against cells containing human-PSA.

In accordance with another aspect of the invention, a method of treating prostate cancer in humans is provided which includes the step of introducing non-human-primate-PSA into a human, wherein a human immune response results in cytotoxic, cell-mediated immunity against cells containing human-PSA.

In accordance with another aspect of the invention, a method of delivering a nucleic acid vaccine expressing a non-human-primate antigen into human cells is provided which includes the steps of administering a quantity of the nucleic acid vaccine to human tissue, and applying electrical fields to the human tissue, whereby the nucleic acid vaccine, expressing non-human-primate antigen, is delivered into cells in the human tissue.

In accordance with another aspect of the invention, a method of inducing an immune response against human PSA in humans is provided which includes the step of introducing a gene sequence derived from a gene of non-human PSA into the human. The non-human PSA gene sequence is expressed as a non-human PSA in the human. The introduced non-human gene sequence comprises a base pair homology to a gene sequence derived from a gene of human PSA, and the homology is in a range of equal to or greater than 88% to less than or equal to 98%. Preferably, the homology is in a range of equal to or greater than 92% to less than or equal to 99%.

In accordance with another aspect of the invention, a DNA vaccine for humans includes is provided which includes a gene sequence derived from a gene of non-human-primate PSA.

In accordance with another aspect of the invention, a method of inducing an immune response against human PSA in humans is provided which includes the step of introducing a non-human PSA into the human, wherein the non-human PSA comprises an amino acid homology to human PSA in a range of equal to or greater than 88% to less than or equal to 98%.

In accordance with another aspect of the invention, a method of inducing an immune response against human PSA in humans is provided which includes the step of introducing a gene sequence derived from a gene of non-human PSA into the human. The non-human PSA gene sequence is expressed as a non-human PSA in the human. The introduced non-human gene sequence comprises a base pair homology to a gene sequence derived from a gene of human PSA, and the homology is in a range of equal to or greater than 88% to less than or equal to 98%. Preferably, the homology is in a range of equal to or greater than 92% to less than or equal to 99%.

In accordance with another aspect of the invention, the use of a vector expressing a non-human-primate antigen is provided for the preparation of a vaccine for administration to humans to provide an immune response against a human antigen. In one respect, the vector is can be a DNA vector. In another respect, the vector can be an RNA vector.

In accordance with another aspect of the invention, the use of a vector expressing a non-human-primate PSA, for the preparation of a vaccine for administration to humans is provided to provide an immune response against human PSA. In one respect, the vector is can be a DNA vector. In another respect, the vector can be an RNA vector.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

Please, incorporate-by-reference, the SEQUENCE LISTING in file 110927 024076 PatentIn ModBJ_ST25.txt, created on Sep. 27, 2011, having a size of 12,681 bytes on CD Copy #1 (CRF). That SEQUENCE LISTING includes SEQUENCE ID NOs. at respective designators <400>.

The invention will be better understood and the above objects as well as objects other than those set forth above will become more apparent after a study of the following detailed description thereof. Such description makes reference to the annexed drawing wherein:

FIGS. 1A, 1B, and 1C set forth cDNA comparisons, derived from the Prior Art, between the cDNA of human PSA, the cDNA of non-human-primate PSA of the Rhesus monkey (*Macaca mulatta*), and the cDNA of non-human-primate PSA of Cynomolgus monkey (*Macaca fasicularis*).

SEQUENCE ID NO. 1 is a DNA sequence which corresponds to *Homo sapiens* extending through FIG. 1A, FIG. 1B, and FIG. 1C.

SEQUENCE ID NO. 2 is a DNA sequence which corresponds to *Macacca mulatta* (Rhesus) extending through FIG. 1A, FIG. 1B, and FIG. 1C.

SEQUENCE ID NO. 3 is a DNA sequence which corresponds to *Macacca fascicularis* (Cynomulgus) extending through FIG. 1A, FIG. 1B, and FIG. 1C.

SEQUENCE ID NO. 4 is a DNA sequence which corresponds to a consensus for primate (*Homo sapiens*, *Macacca mulatta* (Rhesus), and *Macacca fascicularis* (Cynomulgus)) extending through FIG. 1A, FIG. 1B, and FIG. 1C.

FIG. 2 shows that human-PSA is comprised of a sequence of 261 amino acids (in the first section "huPSA"); that Rhesus-monkey-PSA is comprised of a sequence of 261 amino acids (in the first section "rhPSA"). FIG. 2 also shows that the DNA sequence of human-PSA is comprised of a sequence of 786 nucleotides (in the second section "huPSA", Genebank Accession # X73560); that the DNA sequence of Rhesus-monkey-PSA is comprised of a sequence of 786 (in the second section "rhPSA", Genebank Accession # X07730).

SEQUENCE ID NO. 5 is a PRT sequence which corresponds to *Macaca mulatta* (Rhesus) which is the rhPSA sequence shown in FIG. 2.

SEQUENCE ID NO. 6 is a PRT sequence which corresponds to *Homo sapiens* which is the huPSA sequence shown in FIG. 2.

SEQUENCE ID NO. 7 is a DNA sequence which corresponds to *Macaca mulatta* which is the sequence in rhPSA Genebank Accession #X73560 shown in FIG. 2.

SEQUENCE ID NO. 8 is a DNA sequence which corresponds to *Homo sapiens* which is the sequence in huPSA Genebank Accession #X07730 shown in FIG. 2.

Figure 3:
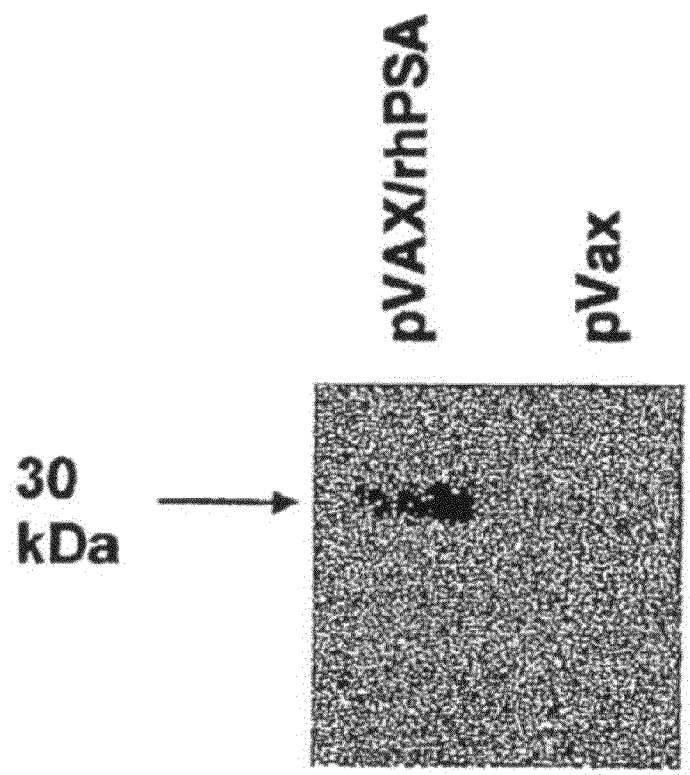

FIG. 3 shows the expression of rhesus PSA in human dendritic cells transduced with pVAX/rhPSA (a plasmid expressing rhesus PSA) and a control plasmid (pVAX).

Figure 4:
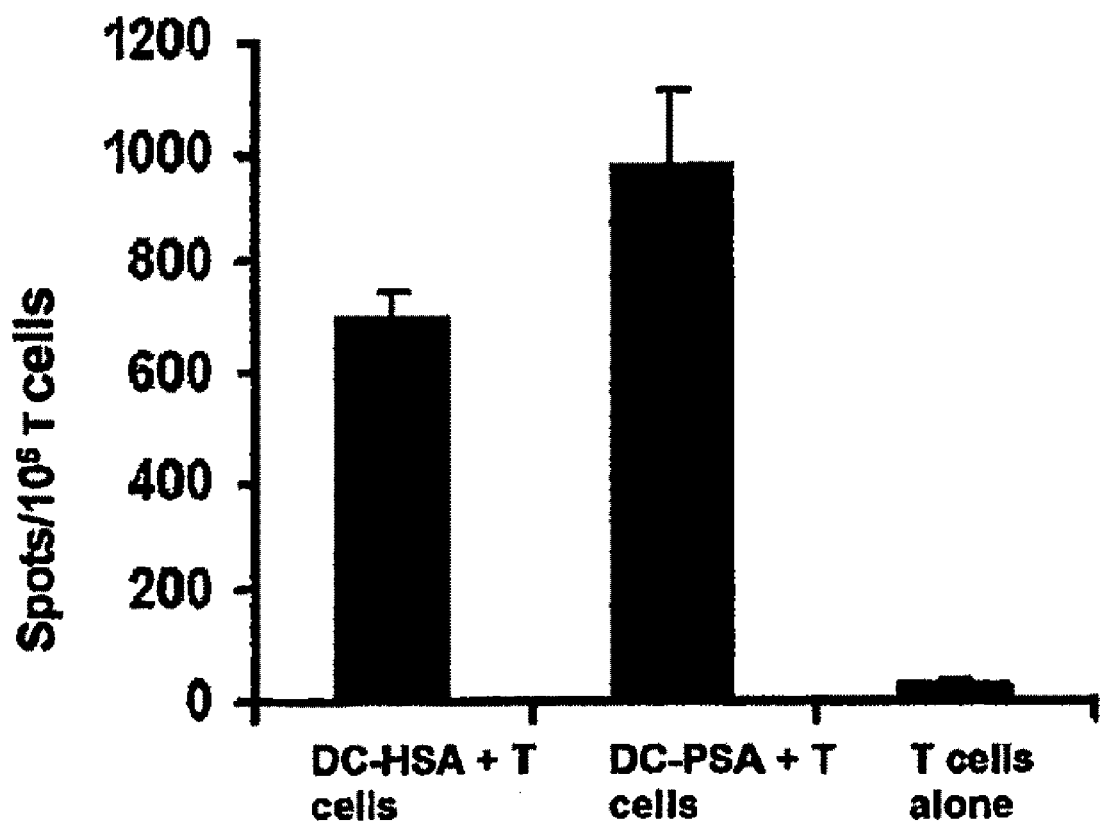

FIG. 4 shows the response of human T cells to stimulation by pVAX/rhPSA transfected monocyte derived human dendritic cells.

MODES FOR CARRYING OUT THE INVENTION

Methods and apparatus are provided for use of a xenogeneic antigen (e.g. protein) in a human, wherein, with respect to the xenogeneic antigen that is used, there are relatively few interspecies differences between the xenogeneic antigen and the human self antigen in order to induce an optimal immune response in the human to its native self antigen.

Relevant interspecies differences are illustrated in FIGS. 1A, 1B, 1C, and 2.

In accordance with one aspect of the invention, a composition of matter is provided which includes non-human-primate-PSA and a pharmaceutically acceptable carrier for administration to humans. See Example 1 below.

In accordance with another aspect of the invention, a vaccine is provided for humans which is comprised of non-human-primate-PSA and a pharmaceutically acceptable carrier for administration to humans. See Example 1 below.

Example 1

Here is a description of steps for making a vaccine formulation containing recombinant non-human primate PSA.

A vaccine formulation containing recombinant non-human primate PSA can be formulated using standard vaccine adjuvants. One formulation can contain 90 mg antigen (recombinant rhesus PSA), 0.7 mg/ml aluminum, and 140 mM sodium chloride. This formulation can be made by the following method.

Three solutions are first made.

First, a 2.1 mg/ml Aluminum hydroxide mixture is made by diluting Alhydrogel (from Accurate Chemical and Scientific Corporation, Westbury N.Y.) to 10 mM MOPS buffer (pH 7.4) to a provide a final-aluminum concentration of 2.1%. The volume of Alhydrogel used in the latter mixture is determined by referring to the insert accompanying the Alhydrogel.

Second, recombinant rhesus PSA is diluted to a final concentration of 270 mg/ml in 10 millimolar MOPS buffer.

Third, a solution of 36 sodium chloride (420 millimolar) in water is prepared.

The first and second solutions (alhydrogel and recombinant rhesus PSA solutions) are mixed in equal volumes (e.g. 1 ml each). The mixture is gently mixed at 4 degrees centigrade by end to end inversion for 30 minutes.

Finally, a volume of sodium chloride equal to the volume of the Alhydrogel solution (e.g. 1 ml) in the mixture is added to dilute the vaccine mixture and to bring the sodium chloride concentration to 140 millimolar. The finally obtained vaccine mixture thus made provides a composition of matter which includes non-human-primate-PSA and a pharmaceutically acceptable carrier for administration to humans.

The production of the recombinant rhesus PSA employed in Example 1 is obtained by expression of recombinant rhesus PSA protein in insect cells. Briefly, a rhPSA gene sequence is cloned into Baculovirus as a fusion gene together with a sequence for a his-tag and a protease signal cleavage site. Recombinant rhPSA protein is produced by transcription and translation.

The recombinant rhPSA protein used in the formulation is purified from Baculovirus-infected insect cell lysates using affinity chromatography, followed by protease cleavage of the his-tag, size exclusion chromatography, and refolding by sequential dialysis. The sequential dialysis can be carried out in decreasing urea concentration buffers.

In accordance with another aspect of the invention, a vaccine is provided wherein the non-human-primate-PSA triggers a human immune response which produces antibodies against human-PSA. See Example 1 above.

In accordance with another aspect of the invention, the use of non-human-primate PSA is provided for the preparation of a vaccine for administration to humans to provide an immune response against human PSA. See Example 1 above.

In accordance with another aspect of the invention, a vaccine is provided wherein a human immune response results in cytotoxic, cell-mediated immunity against human cells which contain human-PSA. See Example 1 above.

In accordance with another aspect of the invention, a method of treating humans includes a step for introducing a vector containing a non-human-primate-DNA sequence into a human for providing expression of non-human-primate-PSA in the human. The vector can be a DNA or RNA vector. Examples of vectors are mammalian expression plasmids, viral RNA or DNA, messenger RNA or other nucleic acid constructs that when introduced into mammalian cells result in the expression of non-human-primate PSA. See Example 2 below.

Example 2

In one method, a DNA vaccine is prepared that contains a plasmid that expresses non-human-primate PSA under the control of a CMV promoter. The plasmid contains other DNA sequences essential to production of the plasmid, such as a bacterial origin of replication and an antibiotic resistance gene such as a Kanamycin resistance gene. The plasmid is mixed at a concentration of 0.5 to five micrograms per microliter in a suitable carrier such as half strength phosphate buffered saline. For administration, the plasmid mixture is loaded into a tuberculin type syringe with a half inch, 27 gauge needle. Twenty to fifty microliters of the plasmid mix are injected intradermally into skin above the deltoid muscle or on the forearm.

Then, an electrode with two parallel rows of needles (0.3 mm diameter needles, 4 mm distance between rows, 1 mm distance between needles in a row, four needles in a row and needle length of 3 mm) is inserted 2-3 mm deep into the skin with a row of needles on each side of the injection site. Electroporation pulses are then applied to the inserted electrode. One pulse protocol consists of two pulses of 1125 V/cm, 50 microsecond duration and 0.125 seconds between pulses followed 0.5 seconds later by eight pulses of 275 V/cm, 10 millisecond duration and 0.125 seconds between pulses.

In accordance with another aspect of the invention, the use of a vector containing a non-human-primate DNA sequence is provided for the preparation of a vaccine for administration to humans to provide an immune response to the antigen in humans. See Example 2 above.

In accordance with another aspect of the invention, the use of vector containing a non-human-primate DNA sequence is provided for the preparation of a vaccine for administration to humans to provide an immune response against human PSA. See Example 2 above.

In accordance with another aspect of the invention, a method of treating prostate cancer in humans is provided which includes the step of introducing non-human-primate-PSA into a human for triggering a human immune response which produces antibodies against human-PSA. See Examples 1 and 2 above for a non-human-primate-PSA and vectors that express non-human-PSA.

In accordance with another aspect of the invention, a method of treating prostate cancer in humans is provided which includes the step of introducing non-human-primate-PSA or vectors that express non-human-PSA into a human, wherein a human immune response results in production of antibodies against human-PSA. See Examples 1 and 2 above for a non-human-primate-PSA and vectors that express non-human-PSA.

In accordance with another aspect of the invention, a method of treating prostate cancer in humans is provided which includes the step of introducing non-human-primate-PSA or vectors that express non-human-PSA into a human for triggering an immune response which includes cytotoxic, cell-mediated immunity against cells containing human-PSA. See Examples 1 and 2 above for a non-human-primate-PSA and vectors that express non-human-PSA.

In accordance with another aspect of the invention, a method of treating prostate cancer in humans is provided which includes the step of introducing non-human-primate-PSA or vectors that express non-human-PSA into a human, wherein a human immune response results in cytotoxic, cell-mediated immunity against cells containing human-PSA. See Examples 1 and 2 above for a non-human-primate-PSA and vectors that express non-human-PSA.

In accordance with another aspect of the invention, a method of delivering a nucleic acid vaccine expressing a non-human-PSA into human cells is provided which includes the steps of administering a quantity of the nucleic acid vaccine to human tissue, and applying electrical fields to the human tissue, whereby the nucleic acid vaccine, expressing non-human-primate antigen, is delivered into cells in the human tissue. See Example 2 above and Example 3 below.

Example 3

Application of electrical fields can be implemented by conducting electroporation techniques. Suitable electroporation techniques are disclosed in U.S. Pat. Nos. 6,010,613, 6,603,998, and 6,713,291, all of which are incorporated herein by reference.

In accordance with another aspect of the invention, a method of delivering a nucleic acid vaccine expressing a non-human-primate PSA into human cells is provided which includes the steps of administering a quantity of the nucleic acid vaccine to human tissue, and applying electrical fields to the human tissue, whereby the nucleic acid vaccine, expressing non-human-primate PSA, is delivered into cells in the human tissue. See Examples 2 and 3 above.

In accordance with another aspect of the invention, a DNA vaccine for humans is provided which includes a gene sequence derived from a gene of non-human-primate PSA.

In accordance with another aspect of the invention, a method of inducing an immune response against human PSA in humans is provided which includes the step of introducing a non-human PSA into the human, wherein the non-human PSA comprises an amino acid homology to human PSA in a range of equal to or greater than 88% to less than or equal to 98%. See Example 1 above for a non-human PSA.

In accordance with another aspect of the invention, a method of inducing an immune response against human PSA in humans is provided which includes the step of introducing a gene sequence derived from a gene of non-human PSA into the human. The non-human PSA gene sequence is expressed as a non-human PSA in the human. The introduced non-human gene sequence comprises a base pair homology to a gene sequence derived from a gene of human PSA, and the homology is in a range of equal to or greater than 88% to less than or equal to 98%. Preferably, the homology is in a range of equal to or greater than 92% to less than or equal to 99%. See Example 2 above.

In accordance with another aspect of the invention, the use of a vector expressing a non-human-primate antigen is provided for the preparation of a vaccine for administration to humans to provide an immune response against a human antigen. In one respect, the vector can be a DNA vector. In another respect, the vector can be an RNA vector. See Example 2 above.

In accordance with another aspect of the invention, the use of a vector expressing a non-human-primate PSA, for the preparation of a vaccine for administration to humans is provided to provide an immune response against human PSA. In one respect, the vector is can be a DNA vector. In another respect, the vector can be an RNA vector. See Example 2 above.

The utility of non-human primate PSA (e.g. rhesus PSA) in the stimulation of the human immune system for attacking human cells that produce human PSA is proved by the evidence illustrated in FIGS. 3 and 4.

FIG. 4 shows the response of human T cells to stimulation by pVAX/rhPSA transfected monocyte derived human dendritic cells. Immature human monocyte dendritic cells were prepared by growth of human monocytes in cytokines. Human monocyte derived dendritic cells were transduced with pVAX/rhPSA. The cells were matured by incubation in medium with poly I:C. After maturation, the cells were used to stimulate autologous human T cells in an in vitro immunization. After two re-stimulations, human PSA specificity was assessed using IFNgamma ELISPOT assay. Specific T cells were compared to T cells stimulated using a, control human serum albumin (HSA). The response shows a human PSA specific T cell response in cells stimulated with the rhesus PSA transduced human dendritic cells. This shows that in an in vitro immunization, the human T cells, stimulated by rhesus PSA, respond in a way indicative of attacking human cells which contain human PSA.

For the above transfection of the human dendritic cells, to demonstrate that in fact the transfected cells were expressing rhesus PSA, a Western blot was done. More specifically, FIG. 3 shows the expression of rhesus PSA in human dendritic cells transduced with pVAX/rhPSA (a plasmid expressing rhesus PSA) and a control plasmid (pVAX). The Western blot shows expression of the expected 30 kilodalton protein for rhesus PSA. For the expression, pVAX/rhPSA and the control plasmid were transduced into immature human dendritic cells by electroporation. Cells were analyzed 24 hours later by Western blot, and the rhesus PSA was detected as a band at 30 kilodaltons.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing new and improved methods and compositions relating to a vaccine against prostate cancer which may advantageously be used to kill prostate cells in a human that have escaped surgical removal of the prostate. With the invention, methods and compositions relating to a vaccine against prostate cancer are provided which cause a triggering of a human immune response that brings about the killing of human cells that produce human-PSA. With the invention, methods and compositions relating to a vaccine against prostate cancer are provided which is not limited to hormonal therapies. With the invention, methods and compositions relating to a vaccine against prostate cancer are provided which use a xenogeneic antigen (e.g. a protein) in a human, wherein, with respect to the xenogeneic antigen that is used, there are relatively few interspecies differences between the xenogeneic antigen and the human self antigen in order to induce an optimal immune response in the human to its native self antigen. With the invention, methods and compositions relating to a vaccine against prostate cancer are provided which use a non-human primate xenogeneic antigen (e.g. a protein) in a human, wherein, with respect to the non-human primate xenogeneic antigen that is used, there are relatively few interspecies differences between the non-human primate xenogeneic antigen and the human self antigen in order to induce an optimal immune response in the human to its native self antigen. With the invention, methods and compositions relating to a vaccine against prostate cancer are provided which use a non-human-primate xenogeneic PSA antigen in a human, wherein, with respect to the non-human-primate xenogeneic PSA antigen that is used, there are relatively few interspecies differences between the non-human-primate xenogeneic PSA antigen and the human self PSA antigen in order to induce an optimal immune response in the human to its native self PSA antigen.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

BIBLIOGRAPHICAL REFERENCES

1. Lundwall, A. and H. Lilja, *Molecular cloning of human prostate specific antigen cDNA*. FEBS Lett, 1987. 214(2): p. 317-22.
2. Greenlee, R. T., et al., *Cancer statistics,* 2000. CA Cancer J Clin, 2000. 50(1): p. 7-33.
3. Richie, J. P., *Anti-androgens and other hormonal therapies for prostate cancer*. Urology, 1999. 54(6A Suppl): p. 15-8.
4. Lord, E. M. and J. G. Frelinger, *Tumor immunotherapy: cytokines and antigen presentation*. Cancer Immunol Immunother, 1998. 46(2): p. 75-81.
5. Rosenberg, S. A., *A new era for cancer immunotherapy based on the genes that encode cancer antigens*. Immunity, 1999. 10(3): p. 281-7.

6. Sanda, M. G., et al., *Recombinant vaccinia-PSA (PROSTVAC) can induce a prostate-specific immune response in androgen-modulated human prostate cancer.* Urology, 1999. 53(2): p. 260-6.
7. Eder, J. P., et al., *A phase I trial of a recombinant vaccinia virus expressing prostate-specific antigen in advanced prostate cancer.* Clin Cancer Res, 2000. 6(5): p. 1632-8.
8. Gulley, J., et al., *Phase I study of a vaccine using recombinant vaccinia virus expressing PSA (rV-PSA) in patients with metastatic androgen-independent prostate cancer.* Prostate, 2002. 53(2): p. 109-17.
9. Kaufman, H. L., et al., *Phase II randomized study of vaccine treatment of advanced prostate cancer (E7897): a trial of the Eastern Cooperative Oncology Group.* J Clin Oncol, 2004. 22(11): p. 2122-32.
10. Meidenbauer, N., et al., *Generation of PSA-reactive effector cells after vaccination with a PSA-based vaccine in patients with prostate cancer.* Prostate, 2000. 43(2): p. 88-100.
11. Barrou, B., et al., *Vaccination of prostatectomized prostate cancer patients in biochemical relapse, with autologous dendritic cells pulsed with recombinant human PSA.* Cancer Immunol Immunother, 2004. 53(5): p. 453-60.
12. Heiser, A., et al., *Autologous dendritic cells transfected with prostate-specific antigen RNA stimulate CTL responses against metastatic prostate tumors.* J Clin Invest, 2002. 109(3): p. 409-17.
13. Davis, M. M., *T cell receptor gene diversity and selection.* Annu Rev Biochem, 1990. 59: p. 475-96.
14. Kappler, J. W., et al., *A T cell receptor V beta segment that imparts reactivity to a class II major histocompatibility complex product.* Cell, 1987. 49(2): p. 263-71.
15. Ramsdell, F., T. Lantz, and B. J. Fowlkes, *A nondeletional mechanism of thymic self tolerance.* Science, 1989. 246 (4933): p. 1038-41.
16. McGargill, M. A., J. M. Derbinski, and K. A. Hogquist, *Receptor editing in developing T cells.* Nat Immunol, 2000. 1(4): p. 336-41.
17. Jameson, S. C., K. A. Hogquist, and M. J. Bevan, *Positive selection of thymocytes.* Annu Rev Immunol, 1995. 13: p. 93-126.
18. Ford, W. L. and J. L. Gowans, *The traffic of lymphocytes.* Semin Hematol, 1969. 6(1): p. 67-83.
19. Mackay, C. R., *Homing of naive, memory and effector lymphocytes.* Curr Opin Immunol, 1993. 5(3): p. 423-7.
20. Sprent, J. and D. F. Tough, *Lymphocyte life-span and memory.* Science, 1994. 265(5177): p. 1395-400.
21. Ferreira, C., et al., *Differential survival of naive CD4 and CD8 T cells.* J Immunol, 2000. 165(7): p. 3689-94.
22. Tanchot, C., et al., *Differential requirements for survival and proliferation of CD8 naive or memory T cells.* Science, 1997. 276(5321): p. 2057-62.
23. Schluns, K. S., et al., *Interleukin-7 mediates the homeostasis of naive and memory CD8 T cells in vivo.* Nat Immunol, 2000. 1(5): p. 426-32.
24. Tan, J. T., et al., *IL-7 is critical for homeostatic proliferation and survival of naive T cells.* Proc Natl Acad Sci USA, 2001. 98(15): p. 8732-7.
25. Ernst, B., et al., *The peptide ligands mediating positive selection in the thymus control T cell survival and homeostatic proliferation in the periphery.* Immunity, 1999. 11(2): p. 173-81.
26. Prlic, M., et al., *Homeostatic expansion occurs independently of costimulatory signals.* J Immunol, 2001. 167(10): p. 5664-8.
27. Banchereau, J. and R. M. Steinman, *Dendritic cells and the control of immunity.* Nature, 1998. 392(6673): p. 245-52.
28. De Smedt, T., et al., *Regulation of dendritic cell numbers and maturation by lipopolysaccharide in vivo.* Exp Med, 1996. 184(4): p. 1413-24.
29. Medzhitov, R. and C. Janeway, Jr., *Innate immune recognition: mechanisms and pathways.* Immunol Rev, 2000. 173: p. 89-97.
30. Kaisho, T., et al., *Endotoxin-induced maturation of MyD88-deficient dendritic cells.* J Immunol, 2001. 166(9): p. 5688-94.
31. Whitmire, J. K. and R. Ahmed, *Costimulation in antiviral immunity: differential requirements for CD4(+) and CD8 (+) T cell responses.* Curr Opin Immunol, 2000. 12(4): p. 448-55.
32. Gajewski, T. F., et al., *Costimulation with B7-1, IL-6, and IL-12 is sufficient for primary generation of murine anti tumor cytolytic T lymphocytes in vitro.* J Immunol, 1995. 154(11): p. 5637-48.
33. Curtsinger, J. M., et al., *Inflammatory cytokines provide a third signal for activation of naive CD4+ and CD8+ T cells.* J Immunol, 1999. 162(6): p. 3256-62.
34. Reis e Sousa, C., et al., *In vivo microbial stimulation induces rapid CD40 ligand-independent production of interleukin 12 by dendritic cells and their redistribution to T cell areas.* J Exp Med, 1997. 186(11): p. 1819-29.
35. Kearney, E. R., et al., *Visualization of peptide-specific T cell immunity and peripheral tolerance induction in vivo.* Immunity, 1994. 1(4): p. 327-39.
36. Veiga-Fernandes, H., et al., *Response of naive and memory CD8+ T cells to antigen stimulation in vivo.* Nat Immunol, 2000. 1(1): p. 47-53.
37. Gudmundsdottir, H., A. D. Wells, and L. A. Turka, *Dynamics and requirements of T cell clonal expansion in vivo at the single-cell level: effector function is linked to proliferative capacity.* J Immunol, 1999. 162(9): p. 5212-23.
38. Murali-Krishna, K., et al., *Counting antigen-specific CD8 T cells: a reevaluation of bystander activation during viral infection.* Immunity, 1998. 8(2): p. 0.177-87.
39. Busch, D. H., et al., *Coordinate regulation of complex T cell populations responding to bacterial infection.* Immunity, 1998. 8(3): p. 353-62.
40. Rocha, B. and H. von Boehmer, *Peripheral selection of the T cell repertoire.* Science, 1991. 251(4998): p. 1225-8.
41. McHeyzer-Williams, M. G. and M. M. Davis, *Antigen-specific development of primary and memory T cells in vivo.* Science, 1995. 268(5207): p. 106-11.
42. Gulbranson-Judge, A. and I. MacLennan, *Sequential antigen-specific growth of T cells in the T zones and follicles in response to pigeon cytochrome c.* Eur J Immunol, 1996. 26(8): p. 1830-7.
43. Zimmerman, C., et al., *Visualization, characterization, and turnover of CD8+ memory T cells in virus-infected hosts.* J Exp Med, 1996. 183(4): p. 1367-75.
44. Schorle, H., et al., *Development and function of T cells in mice rendered interleukin-2 deficient by gene targeting.* Nature, 1991. 352(6336): p. 621-4.
45. Khoruts, A., et al., *A natural immunological adjuvant enhances T cell clonal expansion through a CD28-dependent, interleukin (IL)-2-independent mechanism.* J Exp Med, 1998. 187(2): p. 225-36.
46. Kneitz, B., et al., *Normal clonal expansion but impaired Fas-mediated cell death and anergy induction in interleukin-2-deficient mice.* Eur J Immunol, 1995. 25(9): p. 2572-7.

47. Ku, C. C., et al., *Control of homeostasis of CD8+ memory T cells by opposing cytokines.* Science, 2000. 288(5466): p. 675-8.
48. Leung, D. T., S. Morefield, and D. M. Willerford, *Regulation of lymphoid homeostasis by IL-2 receptor signals in vivo.* J Immunol, 2000. 164(7): p. 3527-34.
49. Lantz, O., et al., *Gamma chain required for naive CD4+ T cell survival but not for antigen proliferation.* Nat Immunol, 2000. 1(1): p. 54-8.
50. Suresh, M., et al., *Role of CD28-B7 interactions in generation and maintenance of CD8 T cell memory.* J Immunol, 2001. 167(10): p. 5565-73.
51. Ranheim, E. A. and T. J. Kipps, *Activated T cells induce expression of B7/BB1 on normal or leukemic B cells through a CD40-dependent signal.* J Exp Med, 1993. 177(4): p. 925-35.
52. Dutton, R. W., L. M. Bradley, and S. L. Swain, *T cell memory.* Annu Rev Immunol, 1998. 16: p. 201-23.
53. Harrington, L. E., et al., *Differentiating between memory and effector CD8 T cells by altered expression of cell surface O-glycans.* J Exp Med, 2000. 191(7): p. 1241-6.
54. Petschner, F., et al., *Constitutive expression of Bcl-xL or Bcl-2 prevents peptide antigen-induced T cell deletion but does not influence T cell homeostasis after a viral infection.* Eur J Immunol, 1998. 28(2): p. 560-9.
55. Lenardo, M., et al., *Mature T lymphocyte apoptosis-immune regulation in a dynamic and unpredictable antigenic environment.* Annu Rev Immunol, 1999. 17: p. 221-53.
56. Refaeli, Y., L. Van Parijs, and A. K. Abbas, *Genetic models of abnormal apoptosis in lymphocytes.* Immunol Rev, 1999. 169: p. 273-82.
57. Refaeli, Y., et al., *Biochemical mechanisms of IL-2-regulated Fas-mediated T cell apoptosis.* Immunity, 1998. 8(5): p. 615-23.
58. Reinhardt, R. L., et al., *Visualizing the generation of memory CD4 T cells in the whole body.* Nature, 2001. 410(6824): p. 101-5.
59. Vella, A. T., et al., *Lipopolysaccharide interferes with the induction of peripheral T cell death.* Immunity, 1995. 2(3): p. 261-70.
60. Opferman, J. T., B. T. Ober, and P. G. Ashton-Rickardt, *Linear differentiation of cytotoxic effectors into memory T lymphocytes.* Science, 1999. 283(5408): p. 1745-8.
61. Jacob, J. and D. Baltimore, *Modelling T-cell memory by genetic marking of memory T cells in vivo.* Nature, 1999. 399(6736): p. 593-7.
62. Murali-Krishna, K., et al., *Persistence of memory CD8 T cells in MHC class I-deficient mice.* Science, 1999. 286(5443): p. 1377-81.
63. Zhang, X., et al., *Potent and selective stimulation of memory-phenotype CD8+ T cells in vivo by IL-15.* Immunity, 1998. 8(5): p. 591-9.
64. Kennedy, M. K., et al., *Reversible defects in natural killer and memory CD8 T cell lineages in interleukin 15-deficient mice.* J Exp Med, 2000. 191(5): p. 771-80.
65. Lodolce, J. P., et al., *T cell-independent interleukin 15Ralpha signals are required for bystander proliferation.* J Exp Med, 2001. 194(8): p. 1187-94.
66. Wang, M. C., et al., *Prostate antigen: a new potential marker for prostatic cancer.* Prostate, 1981. 2(1): p. 89-96.
67. Lilja, H., *A kallikrein-like serine protease in prostatic fluid cleaves the predominant seminal vesicle protein.* J Clin Invest, 1985. 76(5): p. 1899-903.
68. Watt, K. W., et al., *Human prostate-specific antigen: structural and functional similarity with serine proteases.* Proc Natl Acad Sci USA, 1986. 83(10): p. 3166-70.
69. Sensabaugh, G. F., *Isolation and characterization of a semen-specific protein from human seminal plasma: a potential new marker for semen identification.* J Forensic Sci, 1978. 23(1): p. 106-15.
70. Lilja, H. and A. Lundwall, *Molecular cloning of epididymal and seminal vesicular transcripts encoding a semenogelin-related protein.* Proc Natl Acad Sci USA, 1992. 89(10): p. 4559-63.
71. Lilja, H., et al., *Seminal vesicle-secreted proteins and their reactions during gelation and liquefaction of human semen.* J Clin Invest, 1987. 80(2): p. 281-5.
72. Lovgren, J., et al., *Activation of the zymogen form of prostate-specific antigen by human glandular kallikrein 2.* Biochem Biophys Res Commun, 1997. 238(2): p. 549-55.
73. Belanger, A., et al., *Molecular mass and carbohydrate structure of prostate specific antigen: studies for establishment of an international PSA standard.* Prostate, 1995. 27(4): p. 187-97.
74. Catalona, W. J., et al., *Measurement of prostate-specific antigen in serum as a screening test for prostate cancer.* N Engl J Med, 1991. 324(17): p. 1156-61.
75. Chu, T. M., *Prostate-specific antigen in screening of prostate cancer.* J Clin Lab Anal, 1994. 8(5): p. 323-6.
76. Babaian, R. J., et al., *The distribution of prostate specific antigen in men without clinical or pathological evidence of prostate cancer: relationship to gland volume and age.* J Urol, 1992. 147(3 Pt 2): p. 837-40.
77. Stenman, U. H., et al., *A complex between prostate-specific antigen and alpha 1-antichymotrypsin is the major form of prostate-specific antigen in serum of patients with prostatic cancer: assay of the complex improves clinical sensitivity for cancer.* Cancer Res, 1991. 51(1): p. 222-6.
78. Leinonen, J., et al., *Double-label time-resolved immunofluorometric assay of prostate-specific antigen and of its complex with alpha 1-antichymotrypsin.* Clin Chem, 1993. 39(10): p. 2098-103.
79. Lilja, H., et al., *Prostate-specific antigen in serum occurs predominantly in complex with alpha 1-antichymotrypsin.* Clin Chem, 1991. 37(9): p. 1618-25.
80. Nadji, M., et al., *Prostatic-specific antigen: an immunohistologic marker for prostatic neoplasms.* Cancer, 1981. 48(5): p. 1229-32.
81. Wang, M. C., et al., *Purification of a human prostate specific antigen.* Invest Urol, 1979. 17(2): p. 159-63.
82. Papsidero, L. D., et al., *Prostate antigen: a marker for human prostate epithelial cells.* J Natl Cancer Inst, 1981. 66(1): p. 37-42.
83. Lange, P. H., et al., *The value of serum prostate specific-antigen determinations before and after radical prostatectomy.* J Urol, 1989. 141(4): p. 873-9.
84. Oesterling, J. E., et al., *Prostate specific antigen in the preoperative and postoperative evaluation of localized prostatic cancer treated with radical prostatectomy.* J Urol, 1988. 139(4): p. 766-72.
85. Seamonds, B., et al., *Evaluation of prostate-specific antigen and prostatic acid phosphatase as prostate cancer markers.* Urology, 1986. 28(6): p. 472-9.
86. Lightner, D. J., et al., *Prostate specific antigen and local recurrence after radical prostatectomy.* Urol, 1990. 144(4): p. 921-6.
87. Dundas, G. S., A. T. Porter, and P. M. Venner, *Prostate-specific antigen. Monitoring the response of carcinoma of the prostate to radiotherapy with a new tumor marker.* Cancer, 1990. 66(1): p. 45-8.
88. Stamey, T. A., J. N. Kabalin, and M. Ferrari, *Prostate specific antigen in the diagnosis and treatment of adeno-*

88. *carcinoma of the prostate. III. Radiation treated patients.* J Urol, 1989. 141(5): p. 1084-7.
89. Stamey, T. A., et al., *Prostate specific antigen in the diagnosis and treatment of adenocarcinoma of the prostate. IV. Anti-androgen treated patients.* J Urol, 1989. 141 (5): p. 1088-90.
90. Wolff, J. A., et al., *Direct gene transfer into mouse muscle in vivo.* Science, 1990. 247(4949 Pt 1): p. 1465-8.
91. Williams, R. S., et al., *Introduction of foreign genes into tissues of living mice by DNA-coated microprojectiles.* Proc Natl Acad Sci USA, 1991. 88(7): p. 2726-30.
92. Tang, D. C., M. DeVit, and S. A. Johnston, *Genetic immunization is a simple method for eliciting an immune response.* Nature, 1992. 356(6365): p. 152-4.
93. Ulmer, J. B., et al., *Heterologous protection against influenza by injection of DNA encoding a viral protein.* Science, 1993. 259(5102): p. 1745-9.
94. Boshart, M., et al., *A very strong enhancer is located upstream of an immediate early gene of human cytomegalovirus.* Cell, 1985. 41(2): p. 521-30.
95. Pieters, J., *MHC class II restricted antigen presentation.* Curr Opin Immunol, 1997. 9(1): p. 89-96.
96. Jondal, M., R. Schirmbeck, and J. Reimann, *MHC class I-restricted CTL responses to exogenous antigens.* Immunity, 1996. 5(4): p. 295-302.
97. Doe, B., et al., *Induction of cytotoxic T lymphocytes by intramuscular immunization with plasmid DNA is facilitated by bone marrow-derived cells.* Proc Natl Acad Sci USA, 1996. 93(16): p. 8578-83.
98. Twasaki, A., et al., *The dominant role of bone marrow-derived cells in CTL induction following plasmid DNA immunization at different sites.* J Immunol, 1997. 159(1): p. 11-4.
99. Corr, M., et al., *Gene vaccination with naked plasmid DNA: mechanism of CTL priming.* J Exp Med, 1996. 184 (4): p. 1555-60.
100. Condon, C., et al., *DNA-based immunization by in vivo transfection of dendritic cells.* Nat Med, 1996. 2(10): p. 1122-8.
101. Cho, J. H., J. W. Youn, and Y. C. Sung, *Cross-priming as a predominant mechanism for inducing CD8(+) T cell responses in gene gun DNA immunization.* J Immunol, 2001. 167(10): p. 5549-57.
102. Porgador, A., et al., *Predominant role for directly transfected dendritic cells in antigen presentation to CD8+ T cells after gene gun immunization.* Exp Med, 1998. 188(6): p. 1075-82.
103. Corr, M., et al., *In vivo priming by DNA injection occurs predominantly by antigen transfer.* J Immunol, 1999. 163 (9): p. 4721-7.
104. Akbari, O., et al., *DNA vaccination: transfection and activation of dendritic cells as key events for immunity.* J Exp Med, 1999. 189(1): p. 169-78.
105. Rodriguez, F., J. Zhang, and J. L. Whitton, *DNA immunization: ubiquitination of a viral protein enhances cytotoxic T-lymphocyte induction and antiviral protection but abrogates antibody induction.* J Virol, 1997. 71(11): p. 8497-503.
106. Hauser, H. and S. Y. Chen, *Augmentation of DNA vaccine potency through secretory heat shock protein-mediated antigen targeting.* Methods, 2003. 31(3): p. 225-31.
107. Pavlenko, M., et al., *Comparison of PSA-specific CD8 (+) CTL responses and antitumor immunity generated by plasmid DNA vaccines encoding PSA-HSP chimeric proteins.* Cancer Immunol Immunother, 2004. 53(12): p. 1085-1092.
108. Leifert, J. A., et al., *Targeting plasmid-encoded proteins to the antigen presentation pathways.* Immunol Rev, 2004. 199: p. 40-53.
109. Yamamoto, S., et al., *Unique palindromic sequences in synthetic oligonucleotides are required to induce IFN [correction of INF] and augment IFN-mediated [correction of INF] natural killer activity.* J Immunol, 1992. 148(12): p. 4072-6.
110. Krieg, A. M., *CpG motifs in bacterial DNA and their immune effects.* Annu Rev Immunol, 2002. 20: p. 709-60.
111. Krieg, A. M., et al., *CpG motifs in bacterial DNA trigger direct B-cell activation.* Nature, 1995. 374(6522): p. 546-9.
112. Razin, A. and J. Friedman, *DNA methylation and its possible biological roles.* Prog Nucleic Acid Res Mol Biol, 1981. 25: p. 33-52.
113. Cardon, L. R., et al., *Pervasive CpG suppression in animal mitochondrial genomes.* Proc Natl Acad Sci USA, 1994. 91(9): p. 3799-803.
114. Hemmi, H., et al., *A Toll-like receptor recognizes bacterial DNA.* Nature, 2000. 408(6813): p. 740-5.
115. Hornung, V., et al., *Quantitative expression of toll-like receptor 1-10 mRNA in cellular subsets of human peripheral blood mononuclear cells and sensitivity to CpG oligodeoxynucleotides.* J Immunol, 2002. 168(9): p. 4531-7.
116. Bauer, M., et al., *Bacterial CpG-DNA triggers activation and maturation of human CD11c−, CD123+ dendritic cells.* J Immunol, 2001. 166(8): p. 5000-7.
117. Kadowaki, N., et al., *Subsets of human dendritic cell precursors express different toll-like receptors and respond to different microbial antigens.* J Exp Med, 2001. 194(6): p. 863-9.
118. Wagner, H., *Bacterial CpG DNA activates immune cells to signal infectious danger.* Adv Immunol, 1999. 73: p. 329-68.
119. Sparwasser, T., et al., *Macrophages sense pathogens via DNA motifs: induction of tumor necrosis factor-alpha-mediated shock.* Eur J Immunol, 1997. 27(7): p. 1671-9.
120. Sparwasser, T., et al., *Bacterial DNA and immunostimulatory CpG oligonucleotides trigger maturation and activation of murine dendritic cells.* Eur J Immunol, 1998. 28(6): p. 2045-54.
121. Halpern, M. D., R. J. Kurlander, and D. S. Pisetsky, *Bacterial DNA induces murine interferon-gamma production by stimulation of interleukin-12 and tumor necrosis factor-alpha.* Cell Immunol, 1996. 167(1): p. 72-8.
122. Sato, Y., et al., *Immundstimulatory DNA sequences necessary for effective intradermal gene immunization.* Science, 1996. 273(5273): p. 352-4.
123. Spies, B., et al., *Vaccination with plasmid DNA activates dendritic cells via Toll-like receptor 9 (TLR9) but functions in TLR9-deficient mice.* J Immunol, 2003. 171(11): p. 5908-12.
124. Babiuk, S., et al., *TLR9−/− and TLR9+/+ mice display similar immune responses to a DNA vaccine.* Immunology, 2004. 113(1): p. 114-20.
125. Bourgeois, C. and C. Tanchot, *Mini-review CD4 T cells are required for CD8 T cell memory generation.* Eur J Immunol, 2003. 33(12): p. 3225-31.
126. Maecker, H. T., et al., *Cytotoxic T cell responses to DNA vaccination: dependence on antigen presentation via class II MHC.* J Immunol, 1998. 161(12): p. 6532-6.
127. Chan, K., et al., *The roles of MHC class II, CD40, and B7 costimulation in CTL induction by plasmid DNA.* J Immunol, 2001. 166(5): p. 3061-6.

128. Wild, J., et al., *Priming MHC-1-restricted cytotoxic T lymphocyte responses to exogenous hepatitis B surface antigen is CD4+ T cell dependent.* J Immunol, 1999. 163(4): p. 1880-7.
129. Renkvist, N., et al., *A listing of human tumor antigens recognized by T cells.* Cancer Immunol Immunother, 2001. 50(1): p. 3-15.
130. Van Pel, A., et al., *Genes coding for tumor antigens recognized by cytolytic T lymphocytes.* Immunol Rev, 1995. 145: p. 229-50.
131. Gjertsen, M. K., et al., *Vaccination with mutant ras peptides and induction of T-cell responsiveness in-pancreatic carcinoma patients carrying the corresponding RAS mutation.* Lancet, 1995. 346(8987): p. 1399-400.
132. Yanuck, M., et al., *A mutant p53 tumor suppressor protein is a target for peptide-induced CD8+ cytotoxic T-cells.* Cancer Res, 1993. 53(14): p. 3257-61.
133. Boel, P., et al., *BAGE: a new gene encoding an antigen recognized on human melanomas by cytolytic T lymphocytes.* Immunity, 1995. 2(2): p. 167-75.
134. Traversari, C., et al., *A nonapeptide encoded by human gene MAGE-1 is recognized on HLA-A1 by cytolytic T lymphocytes directed against tumor antigen MZ2-E.* J Exp Med, 1992. 176(5): p. 1453-7.
135. Van den Eynde, B., et al., *A new family of genes coding for an antigen recognized by autologous cytolytic T lymphocytes on a human melanoma.* J Exp Med, 1995. 182(3): p. 689-98.
136. Eiben, G. L., et al., *Cervical cancer vaccines: recent advances in HPV research.* Viral Immunol, 2003. 16(2): p. 111-21.
137. Taylor, G. S., *T cell-based therapies for EBV-associated malignancies.* Expert Opin Biol Ther, 2004. 4(1): p. 11-21.
138. Klyushnenkova, E. N., et al., *CD4 and CD8 T-lymphocyte recognition of prostate specific antigen in granulomatous prostatitis.* J. Immunother, 2004. 27(2): p. 136-46.
139. Brichard, V., et al., *The tyrosinase gene codes for an antigen recognized by autologous cytolytic T lymphocytes on HLA-A2 melanomas.* J Exp Med, 1993. 178(2): p. 489-95.
140. Ioannides, C. G., et al., *Cytotoxic T cells isolated from ovarian malignant ascites recognize a peptide derived from the HER-2/neu proto-oncogene.* Cell Immunol, 1993. 151(1): p. 225-34.
141. Vonderheide, R. H., et al., *Characterization of HLA-A3-restricted cytotoxic T lymphocytes reactive against the widely expressed tumor antigen telomerase.* Clin Cancer Res, 2001. 7(11): p. 3343-8.
142. Tsang, K. Y., et al., *Generation of human cytotoxic T cells specific for human carcinoembryonic antigen epitopes from patients immunized with recombinant vaccinia-CEA vaccine.* J Natl Cancer Inst, 1995. 87(13): p. 982-90.
143. Benvenuti, F., M. Cesco-Gaspere, and O. R. Burrone, *Anti-idiotypic DNA vaccines for B-cell lymphoma therapy.* Front Biosci, 2002. 7: p. d228-34.
144. Di Carlo, E., et al., *Inhibition of mammary carcinogenesis by systemic interleukin 12 or p185neu DNA vaccination in Her-2/neu transgenic BALB/c mice.* Clin Cancer Res, 2001. 7(3 Suppl): p. 830s-837s.
145. Niethammer, A. G., et al., *A DNA vaccine against VEGF receptor 2 prevents effective angiogenesis and inhibits tumor growth.* Nat Med, 2002. 8(12): p. 1369-75.
146. Bright, R. K., et al., *Protection against a lethal challenge with SV40-transformed cells by the direct injection of DNA-encoding SV40 large tumor antigen.* Cancer Res, 1996. 56(5): p. 1126-30.
147. Ross, H. M., et al., *Priming for T-cell-mediated rejection of established tumors by cutaneous DNA immunization.* Clin Cancer Res, 1997. 3(12 Pt 1): p. 2191-6.
148. Conry, R. M., et al., *A carcinoembryonic antigen polynucleotide vaccine has in vivo antitumor activity.* Gene Ther, 1995. 2(1): p. 59-65.
149. Tuting, T., et al., *Induction of tumor antigen-specific immunity using plasmid DNA immunization in mice.* Cancer Gene Ther, 1999. 6(1): p. 73-80.
150. Roos, A. K., et al., *Induction of PSA-specific CTLs and anti-tumor immunity by a genetic prostate cancer vaccine.* Prostate, 2005. 62(3): p. 217-23.
151. Zhou, H., et al., *A novel transgenic mouse model for immunological evaluation of carcinoembryonic antigen-based DNA minigene vaccines.* J Clin Invest, 2004. 113(12): p. 1792-8.
152. Piechocki, M. P., et al., *Human ErbB-2 (Her-2) transgenic mice: a model system for testing Her-2 based vaccines.* J Immunol, 2003. 171(11): p. 5787-94.
153. Rosato, A., et al., *CTL response and protection against P815 tumor challenge in mice immunized with DNA expressing the tumor-specific antigen P815A.* Hum Gene Ther, 1997. 8(12): p. 1451-8.
154. Bowne, W. B., et al., *Coupling and uncoupling of tumor immunity and autoimmunity.* J Exp Med, 1999. 190(11): p. 1717-22.
155. Van den Eynde, B., et al., *The gene coding for a major tumor rejection antigen of tumor P815 is identical to the normal gene of syngeneic DBA/2 mice.* J Exp Med, 1991. 173(6): p. 1373-84.
156. Ercolini, A. M., et al., *Identification and characterization of the immunodominant rat HER-2/neu MHC class I epitope presented by spontaneous mammary tumors from HER-2/neu-transgenic mice.* J Immunol, 2003. 170(8): p. 4273-80.
157. Nagata, Y., et al., *Peptides derived from a wild-type murine proto-oncogene c-erbB-2/HER2/neu can induce CTL and tumor suppression in syngeneic hosts. Sequences of murine c-erbB-2, human Her2 and rat neu antigens.* J Immunol, 1997. 159(3): p. 1336-43.
158. Weber, L. W., et al., *Tumor immunity and autoimmunity induced by immunization with homologous DNA.* Clin Invest, 1998. 102(6): p. 1258-64.
159. Hawkins, W. G., et al., *Immunization with DNA coding for gp100 results in CD4 T-cell independent antitumor immunity.* Surgery, 2000. 128(2): p. 273-80.
160. Guevara-Patino, J. A., et al., *Immunity to cancer through immune recognition of altered self: studies with melanoma.* Adv Cancer Res, 2003. 90: p. 157-77.
161. Overwijk, W. W., et al., *gp100/pmel 17 is a murine tumor rejection antigen: induction of "self"-reactive, tumoricidal T cells using high-affinity, altered peptide ligand.* J Exp Med, 1998. 188(2): p. 277-86.
162. Gold, J. S., et al., *A single heteroclitic epitope determines cancer immunity after xenogeneic DNA immunization against a tumor differentiation antigen.* J Immunol, 2003. 170(10): p. 5188-94.
163. Wolchok, J. D., et al., *DNA vaccines: an active immunization strategy for prostate cancer.* Semin Oncol, 2003. 30(5): p. 659-66.
164. Hassett, D. E., et al., *Direct ex vivo kinetic and phenotypic analyses of CD8(+) T-cell responses induced by DNA immunization.* J Virol, 2000. 74(18): p. 8286-91.
165. Kwissa, M., et al., *Cytokine-facilitated priming of CD8 (+) T cell responses by DNA vaccination.* J Mol Med, 2003. 81(2): p. 91-101.

166. Denis-Mize, K. S., et al., *Plasmid DNA adsorbed onto cationic microparticles mediates target gene expression and antigen presentation by dendritic cells.* Gene Ther, 2000. 7(24): p. 2105-12.

167. O'Hagan, D., et al., *Induction of potent immune responses by cationic microparticles with adsorbed human immunodeficiency virus DNA vaccines.* J Virol, 2001. 75(19): p. 9037-43.

168. Drabick, J. J., et al., *Cutaneous transfection and immune responses to intradermal nucleic acid vaccination are significantly enhanced by in vivo electropermeabilization.* Mol Ther, 2001. 3(2): p. 249-55.

169. Quaglino, E., et al., *Electroporated DNA vaccine clears away multifocal mammary carcinomas in her-2/neu transgenic mice.* Cancer Res, 2004. 64(8): p. 2858-64.

170. Mir, L. M., et al., *High-efficiency gene transfer into skeletal muscle mediated by electric pulses.* Proc Natl Acad Sci USA, 1999. 96(8): p. 4262-7.

171. Widera, G., et al., *Increased DNA vaccine delivery and immunogenicity by electroporation in vivo.* J Immunol, 2000. 164(9): p. 4635-40.

172. Maloy, K. J., et al., *Intralymphatic immunization enhances DNA vaccination.* Proc Natl Acad Sci USA, 2001. 98(6): p. 3299-303.

173. Leder, C., et al., *Enhancement of capsid gene expression: preparing the human papillomavirus type 16 major structural gene L1 for DNA vaccination purposes.* J Virol, 2001. 75(19): p. 9201-9.

174. Liu, W. J., et al., *Codon modified human papillomavirus type 16 E7 DNA vaccine enhances cytotoxic T-lymphocyte induction and anti-tumour activity.* Virology, 2002. 301 (1): p. 43-52.

175. Chen, C. H., et al., *Enhancement of DNA vaccine potency by linkage of antigen gene to an HSP70 gene.* Cancer Res, 2000. 60(4): p. 1035-42.

176. Stevenson, F. K., et al., *DNA vaccines to attack cancer.* Proc Natl Acad Sci USA, 2004. 101 Suppl 2: p. 14646-52.

177. Rodriguez, F., et al., *Immunodominance in virus-induced CD8(+) T-cell responses is dramatically modified by DNA immunization and is regulated by gamma interferon.* J Virol, 2002. 76(9): p. 4251-9.

178. Deng, Y., et al., *MHC affinity, peptide liberation, T cell repertoire, and immunodominance all contribute to the paucity of MHC class I-restricted peptides recognized by antiviral CTL.* J Immunol, 1997. 158(4): p. 1507-15.

179. Rice, J., et al., *DNA fusion vaccine designed to induce cytotoxic T cell responses against defined peptide motifs: implications for cancer vaccines.* J Immunol, 2001. 167 (3): p. 1558-65.

180. Rice, J., S. Buchan, and F. K. Stevenson, *Critical components of a DNA fusion vaccine able to induce protective cytotoxic T cells against a single epitope of a tumor antigen.* J Immunol, 2002. 169(7): p. 3908-13.

181. Klinman, D. M., et al., *Use of CpG oligodeoxynucleotides as immune adjuvants.* Immunol Rev, 2004. 199: p. 201-16.

182. Klinman, D. M., G. Yamshchikov, and Y. Ishigatsubo, *Contribution of CpG motifs to the immunogenicity of DNA vaccines.* J Immunol, 1997. 158(8): p. 3635-9.

183. Takeshita, F., et al., *Cutting edge: Role of Toll-like receptor 9 in CpG DNA-induced activation of human cells.* J Immunol, 2001. 167(7): p. 3555-8.

184. Conry, R. M., et al., *Selected strategies to augment polynucleotide immunization.* Gene Ther, 1996. 3(1): p. 67-74.

185. Pasquini, S., et al., *Cytokines and costimulatory molecules as genetic adjuvants.* Immunol Cell Biol, 1997. 75(4): p. 397-401.

186. Song, K., Y. Chang, and G. J. Prud'homme, *IL-12 plasmid-enhanced DNA vaccination against carcinoembryonic antigen (CEA) studied in immune-gene knockout mice.* Gene Ther, 2000. 7(18): p. 1527-35.

187. Kwissa, M., et al., *Cytokine-facilitated priming of CD8+ T cell responses by DNA vaccination.* J Mol Med, 2003. 81(2): p. 91-101.

188. Bowne, W. B., et al., *Injection of DNA encoding granulocyte-macrophage colony-stimulating factor recruits dendritic cells for immune adjuvant effects.* Cytokines Cell Mol Ther, 1999. 5(4): p. 217-25.

189. Pertmer, T. M., et al., *Gene gun-based nucleic acid immunization: elicitation of humoral and cytotoxic T lymphocyte responses following epidermal delivery of nanogram quantities of DNA.* Vaccine, 1995. 13(15): p. 1427-30.

190. Haynes, J. R., *Particle-mediated DNA vaccine delivery to the skin.* Expert Opin Biol Ther, 2004. 4(6): p. 889-900.

191. O'Hagan, D. T., M. Singh, and J. B. Ulmer, *Microparticles for the delivery of DNA vaccines.* Immunol Rev, 2004. 199: p. 191-200.

192. Davis, H. L., et al., *Direct gene transfer in skeletal muscle: plasmid DNA-based immunization against the hepatitis B virus surface antigen.* Vaccine, 1994. 12(16): p. 1503-9.

193. Trimble, C., et al., *Comparison of the CD8+ T cell responses and antitumor effects generated by DNA vaccine administered through gene gun, biojector, and syringe.* Vaccine, 2003. 21(25-26): p. 4036-42.

194. Schneeberger, A., et al., *CpG motifs are efficient adjuvants for DNA cancer vaccines.* J Invest Dermatol, 2004. 123(2): p. 371-9.

195. Chattergoon, M. A., et al., *Co-immunization with plasmid IL-12 generates a strong T-cell memory response in mice.* Vaccine, 2004. 22(13-14): p. 1744-50.

196. Kim, J. J., et al., *Engineering of in vivo immune responses to DNA immunization via codelivery of costimulatory molecule genes.* Nat Biotechnol, 1997. 15(7): p. 641-6.

197. Kim, J. J., et al., *Engineering DNA vaccines via co-delivery of co-stimulatory molecule genes.* Vaccine, 1998. 16(19): p. 1828-35.

198. Kim, J. J., et al., *Chemokine gene adjuvants can modulate immune responses induced by DNA vaccines.* J Interferon Cytokine Res, 2000. 20(5): p. 487-98.

199. Sumida, S. M., et al., *Recruitment and expansion of dendritic cells in vivo potentiate the immunogenicity of plasmid DNA vaccines.* J Clin Invest, 2004. 114(9): p. 1334-42.

200. Badovinac, V. P. and J. T. Harty, *Memory lanes.* Nat Immunol, 2003. 4(3): p. 212-3.

201. Kaech, S. M., et al., *Selective expression of the interleukin 7 receptor identifies effector CD8 T cells that give rise to long-lived memory cells.* Nat Immunol, 2003. 4(12): p. 1191-8.

202. Wherry, E. J., et al., *Lineage relationship and protective immunity of memory CD8 T cell subsets.* Nat Immunol, 2003. 4(3): p. 225-34.

203. Zinkernagel, R. M., et al., *On immunological memory.* Annu Rev Immunol, 1996. 14: p. 333-67.

204. Ochsenbein, A. F., et al., *Immune surveillance against a solid tumor fails because of immunological ignorance.* Proc Natl Acad Sci USA, 1999. 96(5): p. 2233-8.

205. Zinkernagel, R. M., *Immunity against solid tumors?* Int J Cancer, 2001. 93(1): p. 1-5.
206. Speiser, D.-E., et al., *Self antigens expressed by solid tumors Do not efficiently stimulate naive or activated T cells: implications for immunotherapy.* J Exp Med, 1997. 186(5): p. 645-53.
207. Kursar, M., et al., *Regulatory CD4+ CD25+ T cells restrict memory CD8+ T cell responses.* J Exp Med, 2002. 196(12): p. 1585-92.
208. Robinson, H. L., *Prime boost vaccines power up in people.* Nat Med, 2003. 9(6): p. 642-3.
209. McConkey, S. J., et al., *Enhanced T-cell immunogenicity of plasmid DNA vaccines boosted by recombinant modified vaccinia virus Ankara in humans.* Nat Med, 2003. 9(6): p. 729-35.
210. Kim, J. J., et al., *Induction of immune responses and safety profiles in rhesus macaques immunized with a DNA vaccine expressing human prostate specific antigen.* Oncogene, 2001. 20(33): p. 4497-506.
211. Pavlenko, M., et al., *A phase I trial of DNA vaccination with a plasmid expressing prostate-specific antigen in patients with hormone-refractory prostate cancer.* Br J Cancer, 2004. 91(4): p. 688-94.
212. Conry, R. M., et al., *Safety and immunogenicity of a DNA vaccine encoding carcinoembryonic antigen and hepatitis B surface antigen in colorectal carcinoma patients.* Clin Cancer Res, 2002. 8(9): p. 2782-7.
213. Klencke, B., et al., *Encapsulated plasmid DNA treatment for human papillomavirus 16-associated anal dysplasia: a Phase I study of ZYC101.* Clin Cancer Res, 2002. 8(5): p. 1028-37.
214. Timmerman, J. M., et al., *Immunogenicity of a plasmid DNA vaccine encoding chimeric idiotype in patients with B-cell lymphoma.* Cancer Res, 2002. 62(20): p. 5845-52.
215. Rosenberg, S. A., et al., *Inability to immunize patients with metastatic melanoma using plasmid DNA encoding the gp100 melanoma-melanocyte antigen.* Hum Gene Ther, 2003. 14(8): p. 709-14.
216. Tagawa, S. T., et al., *Phase I study of intranodal delivery of a plasmid DNA vaccine for patients with Stage IV melanoma.* Cancer, 2003. 98(1): p. 144-54.
217. Mincheff, M., et al., *Naked DNA and adenoviral immunizations for immunotherapy of prostate cancer: a phase I/II clinical trial.* Eur Urol, 2000. 38(2): p. 208-17.
218. Rosenberg, S. A., et al., *Recombinant fowlpox viruses encoding the anchor-modified gp100 melanoma antigen can generate antitumor immune responses in patients with metastatic melanoma.* Clin Cancer Res, 2003. 9(8): p. 2973-80.
219. Hollon, T., *Researchers and regulators reflect on first gene therapy death.* Nat Med, 2000. 6(1): p. 6.
220. Krieg, A. M., *Antitumor applications of stimulating toll-like receptor 9 with CpG oligodeoxynucleotides.* Curr Oncol Rep, 2004. 6(2): p. 88-95.
221. Matsuo, H., et al., *Peptide-selected T cell lines from myasthenia gravis patients and controls recognize epitopes that are not processed from whole acetylcholine receptor.* J Immunol, 1995. 155(7): p. 3683-92.
222. Vitiello, A., et al., *Comparison of cytotoxic T lymphocyte responses induced by peptide or DNA immunization: implications on immunogenicity and immunodominance.* Eur J Immunol, 1997. 27(3): p. 671-8.
223. Xue, B. H., et al., *Induction of human cytotoxic T lymphocytes specific for prostate-specific antigen.* Prostate, 1997. 30(2): p. 73-8.
224. Alexander, R. B., *Induction of human cytotoxic T lymphocytes specific for prostate-specific antigen.* Prostate, 1997. 32(1): p. 73-4.
225. Chakraborty, N. G., et al., *Recognition of PSA-derived peptide antigens by T cells from prostate cancer patients without any prior stimulation.* Cancer Immunol Immunother, 2003. 52(8): p. 497-505.
226. Alexander, R. B., et al., *Specific T cell recognition of peptides derived from prostate-specific antigen in patients with prostate cancer.* Urology, 1998. 51(1): p. 150-7.
227. Correale, P., et al., *Generation of human cytolytic T lymphocyte lines directed against prostate-specific antigen (PSA) employing a PSA oligoepitope peptide.* J Immunol, 1998. 161(6): p. 3186-94.
228. Perambakam, S., et al., *Induction of Tc2 cells with specificity for prostate-specific antigen from patients with hormone-refractory prostate cancer.* Cancer Immunol Immunother, 2002. 51(5): p. 263-70.
229. Correale, P., et al., *In vitro generation of human cytotoxic T lymphocytes specific for peptides derived from prostate-specific antigen.* J Natl Cancer Inst, 1997. 89(4): p. 293-300.
230. Corman, J. M., E. E. Sercarz, and N. K. Nanda, *Recognition of prostate-specific antigenic peptide determinants by human CD4 and CD8 T cells.* Clin Exp Immunol, 1998. 114(2): p. 166-72.
231. Harada, M., et al., *Prostate-specific antigen-derived epitopes capable of inducing cellular and humoral responses in HLA-A24+ prostate cancer patients.* Prostate, 2003. 57(2): p. 152-9.
232. Berlyn, K. A., et al., *Generation of CD4(+) and CD8(+) T lymphocyte responses by dendritic cells armed with PSA/anti-PSA (antigen/antibody) complexes.* Clin Immunol, 2001. 101(3): p. 276-83.
233. Heiser, A., et al., *Human dendritic cells transfected with renal tumor RNA stimulate polyclonal T-cell responses against antigens expressed by primary and metastatic tumors.* Cancer Res, 2001. 61(8): p. 3388-93.
234. Ozenci, V., et al., *Presence and specificity of tumor associated lymphocytes from ascites fluid in prostate cancer.* Prostate, 2005.
235. Rini, B. I., et al., *Prostate-specific antigen kinetics as a measure of the biologic effect of granulocyte-macrophage colony-stimulating factor in patients with serologic progression of prostate cancer.* J Clin Oncol, 2003. 21(1): p. 99-105.
236. Freedland, S. J., et al., *Immunotherapy of prostate cancer.* Curr Urol Rep, 2001. 2(3): p. 242-7.
237. Olsson, A. Y., H. Lilja, and A. Lundwall, *Taxon-specific evolution of glandular kallikrein genes and identification of a progenitor of prostate-specific antigen.* Genomics, 2004. 84(1): p. 147-56.
238. Yousef, G. M. and E. P. Diamandis, *The new human tissue kallikrein gene family: structure, function, and association to disease.* Endocr Rev, 2001. 22(2): p. 184-204.
239. Young, C. Y., et al., *Tissue-specific and hormonal regulation of human prostate-specific glandular kallikrein.* Biochemistry, 1992. 31(3): p. 818-24.
240. Wolf, D. A., P. Schulz, and F. Fittler, *Transcriptional regulation of prostate kallikrein-like genes by androgen.* Mol Endocrinol, 1992. 6(5): p. 753-62.
241. Karr, J. F., et al., *The presence of prostate-specific antigen-related genes in primates and the expression of recombinant human prostate-specific antigen in a transfected murine cell line.* Cancer Res, 1995. 55(11): p. 2455-62.

242. Gauthier, E. R., et al., *Characterization of rhesus monkey prostate specific antigen cDNA*. Biochim Biophys Acta, 1993. 1174(2): p. 207-10.
243. Olsson, A. Y. and A. Lundwall, *Organization and evolution of the glandular kallikrein locus in Mus musculus*. Biochem Biophys Res Commun, 2002. 299(2): p. 305-11.
244. van Leeuwen, B. H., et al., *Mouse glandular kallikrein genes. Identification, structure, and expression of the renal kallikrein gene*. J Biol Chem, 1986. 261(12): p. 5529-35.
245. Evans, B. A., C. C. Drinkwater, and R. I. Richards, *Mouse glandular kallikrein genes. Structure and partial sequence analysis of the kallikrein gene locus*. J Biol Chem, 1987. 262(17): p. 8027-34.
246. Wei, C., et al., *Expression of human prostate-specific antigen (PSA) in a mouse tumor cell line reduces tumorigenicity and elicits PSA-specific cytotoxic T lymphocytes*. Cancer Immunol Immunother, 1996. 42(6): p. 362-8.
247. Elzey, B. D., et al., *Immunization with type 5 adenovirus recombinant for a tumor antigen in combination with recombinant canarypox virus (ALVAC) cytokine gene delivery induces destruction of established prostate tumors*. Int J Cancer, 2001. 94(6): p. 842-9.
248. Kim, J. J., et al., *Molecular and immunological analysis of genetic prostate specific antigen (PSA) vaccine*. Oncogene, 1998. 17(24): p. 3125-35.
249. Willis, R. A., et al., *Dendritic cells transduced with HSV-1 amplicons expressing prostate-specific antigen generate antitumor immunity in mice*. Hum Gene Ther, 2001. 12(15): p. 1867-79.
250. Wei, C., et al., *Tissue-specific expression of the human prostate-specific antigen gene in transgenic mice: implications for tolerance and immunotherapy*. Proc Natl Acad Sci USA, 1997. 94(12): p. 6369-74.
251. Nossal, G. J., *Negative selection of lymphocytes*. Cell, 1994. 76(2): p. 229-39.
252. Turner, M. J., et al., *T-cell antigen discovery (T-CAD) assay: a novel technique for identifying T cell epitopes*. J Immunol Methods, 2001. 256(1-2): p. 107-19.
253. Vitiello, A., et al., *Analysis of the HLA-restricted influenza-specific cytotoxic T lymphocyte response in transgenic mice carrying a chimeric human-mouse class I major histocompatibility complex*. J Exp Med, 1991. 173(4): p. 1007-15.
254. Wentworth, P. A., et al., *Differences and similarities in the A2.1-restricted cytotoxic T cell repertoire in humans and human leukocyte antigen-transgenic mice*. Eur J Immunol, 1996. 26(1): p. 97-101.
255. Alexander, J., et al., *Derivation of HLA-A11/Kb transgenic mice: functional CTL repertoire and recognition of human A11-restricted CTL epitopes*. J Immunol, 1997. 159(10): p. 4753-61.
256. Gotoh, M., et al., *Development of HLA-A2402/K(b) transgenic mice*. Int J Cancer, 2002. 100(5): p. 565-70.
257. Ciupitu, A. M., et al., *Immunization with a lymphocytic choriomeningitis virus peptide mixed with heat shock protein 70 results in protective antiviral immunity and specific cytotoxic T lymphocytes*. J Exp Med, 1998. 187(5): p. 685-91.
258. Suto, R. and P. K. Srivastava, *A mechanism for the specific immunogenicity of heat shock protein-chaperoned peptides*. Science, 1995. 269(5230): p. 1585-8.
259. Suzue, K., et al., *Heat shock fusion proteins as vehicles for antigen delivery into the major histocompatibility complex class I presentation pathway*. Proc Natl Acad Sci USA, 1997. 94(24): p. 13146-51.
260. Hsu, K. F., et al., *Enhancement of suicidal DNA vaccine potency by linking Mycobacterium tuberculosis heat shock protein 70 to an antigen*. Gene Ther, 2001. 8(5): p. 376-83.
261. Barrios, C., et al., *Heat shock proteins as carrier molecules: in vivo helper effect mediated by Escherichia coli GroEL and DnaK proteins requires cross-linking with antigen*. Clin Exp Immunol, 1994. 98(2): p. 229-33.
262. Chu, N. R., et al., *Immunotherapy of a human papillomavirus (HPV) type 16 E7-expressing tumour by administration of fusion protein comprising Mycobacterium bovis bacille Calmette-Guerin (BCG) hsp65 and HPV16 E7*. Clin Exp Immunol, 2000. 121(2): p. 216-25.
263. Udono, H., et al., *Generation of cytotoxic T lymphocytes by MHC class I ligands fused to heat shock cognate protein 70*. Int Immunol, 2001. 13(10): p. 1233-42.
264. McCormack, R. T., et al., *Molecular forms of prostate-specific antigen and the human kallikrein gene family: a new era*. Urology, 1995. 45(5): p. 729-44.
265. Planelles, L., et al., *DNA immunization with Trypanosoma cruzi HSP70 fused to the KMP11 protein elicits a cytotoxic and humoral immune response against the antigen and leads to protection*. Infect Immun, 2001. 69(10): p. 6558-63.
266. Michel, N., et al., *Enhanced immunogenicity of HPV 16 E7 fusion proteins in DNA vaccination*. Virology, 2002. 294(1): p. 47-59.
267. Ohashi, P. S., et al., *Ablation of "tolerance" and induction of diabetes by virus infection in viral antigen transgenic mice*. Cell, 1991. 65(2): p. 305-17.
268. Grossmann, M. E., E. Davila, and E. Celis, *Avoiding Tolerance Against Prostatic Antigens With Subdominant Peptide Epitopes*. J Immunother, 2001. 24(3): p. 237-241.
269. Gross, D. A., et al., *High vaccination efficiency of low-affinity epitopes in antitumor immunotherapy*. J Clin Invest, 2004. 113(3): p. 425-33.
270. Schirle, M., T. Weinschenk, and S. Stevanovic, *Combining computer algorithms with experimental approaches permits the rapid and accurate identification of T cell epitopes from defined antigens*. J Immunol Methods, 2001. 257(1-2): p. 1-16.
271. Rammensee, H., et al., *SYFPEITHI: database for MHC ligands and peptide motifs*. Immunogenetics, 1999. 50(3-4): p. 213-9.
272. Gairin, J. E., et al., *Optimal lymphocytic choriomeningitis virus sequences restricted by H-2 Db major histocompatibility complex class I molecules and presented to cytotoxic T lymphocytes*. J Virol, 1995. 69(4): p. 2297-305.
273. Zhang, W., et al., *Crystal structure of the major histocompatibility complex class I H-2 Kb molecule containing a single viral peptide: implications for peptide binding and T-cell receptor recognition*. Proc Natl Acad Sci USA, 1992. 89(17): p. 8403-7.
274. Hacker, H., et al., *Immune cell activation by bacterial CpG-DNA through myeloid differentiation marker 88 and tumor necrosis factor receptor-associated factor (TRAF)6*. J Exp Med, 2000. 192(4): p. 595-600.
275. Zelenay, S., F. Elias, and J. Flo, *Immunostimulatory effects of plasmid DNA and synthetic oligodeoxynucleotides*. Eur J Immunol, 2003. 33(5): p. 1382-92.
276. Chace, J. H., et al., *Bacterial DNA-induced NK cell IFN-gamma production is dependent on macrophage secretion of IL-12*. Clin Immunol Immunopathol, 1997. 84(2): p. 185-93.
277. Cowdery, J. S., et al., *Bacterial DNA induces NK cells to produce IFN-gamma in vivo and increases the toxicity of lipopolysaccharides*. J Immunol, 1996. 156(12): p. 4570-5.

What is claimed is:

1. A method of treating prostate cancer in humans, consisting essentially of the step of introducing a DNA vector expressing Rhesus-PSA (prostate-specific antigen) comprising SEQUENCE ID NO. 5 into a human for triggering a human immune response against human PSA (prostate-specific antigen).

2. The method of claim 1 for treating prostate cancer in humans, consisting essentially of the step of introducing a DNA vector expressing Rhesus-PSA (prostate-specific antigen) comprising SEQUENCE ID NO. 5 into a human, wherein a human immune response results in production of antibodies against human-PSA (prostate-specific antigen).

3. The method of claim 1 for treating prostate cancer in humans, consisting essentially of the step of introducing a DNA vector expressing Rhesus-PSA (prostate-specific antigen) comprising SEQUENCE ID NO.5 into a human for triggering an immune response which includes cytotoxic, cell-mediated immunity against cells containing human-PSA (prostate-specific antigen).

4. A method of delivering a nucleic acid vaccine expressing a Rhesus PSA (prostate-specific antigen) into human cells in tissue in a human patient for treating prostate cancer, consisting essentially of the steps of:
 administering a quantity of the nucleic acid vaccine expressing Rhesus PSA (prostate-specific antigen), comprising SEQUENCE ID NO. 5, to the human tissue in the human patient at an administration site, and
 applying electrical fields to the human tissue in the human patient at the administration site, whereby the nucleic acid vaccine is delivered into cells in the human tissue for treating the prostate cancer.

* * * * *

SEQUENCE LISTING

<160> NUMBER OF SEQ ID NOS: 8

<210> SEQ ID NO 1
<211> LENGTH: 903
<212> TYPE: DNA
<213> ORGANISM: Homo sapiens

<400> SEQUENCE: 1

```
gggggagccc caagcttacc acctgcaccc ggagagctgt gtcaccatgt gggtcccggt       60
tgtcttcctc accctgtccg tgacgtggat tggtgctgca ccctcatcc tgtctcggat      120
tgtgggaggc tgggagtgcg agaagcattc ccaaccctgg caggtgcttg tggcctctcg      180
tggcagggca gtctgcggcg tgttctggt gcaccccag tgggtcctca cagctgccca      240
ctgcatcagg aacaaaagcg tgatcttgct gggtcggcac agcctgtttc atcctgaaga      300
cacaggccag gtatttcagg tcagccacag cttcccacac ccgctctacg atatgagcct      360
cctgaagaat cgattcctca ggccaggtga tgactccagc cacgacctca tgctgctccg      420
cctgtcagag cctgccgagc tcacggatgc tgtgaaggtc atggaccgc ccacccagga      480
gccagcactg ggaccacct gctacgcctc aggctggggc agcattgaac cagaggagtt      540
cttgacccca aagaaacttc agtgtgtgga cctccatgtt atttccaatg acgtgtgtgc      600
gcaagttcac cctcagaagg tgaccaagtt catgctgtgt gctggacgct ggacagggg      660
caaaagcacc tgctcgggtg attctggggg cccacttgtc tgtaatggtg tgcttcaagg      720
tatcacgtca tggggcagtg aaccatgtgc cctgccgaa aggccttccc tgtacaccaa      780
ggtggtgcat taccggaagt ggatcaagga caccatcgtg ccaacccct gagcacccct      840
atcaactccc tattgtagta aacttggaac cttggaaatg accaggccaa gactcaggcc      900
tcc                                                                    903
```

<210> SEQ ID NO 2
<211> LENGTH: 945
<212> TYPE: DNA
<213> ORGANISM: Macaca mulatta

<400> SEQUENCE: 2

```
ctcaccgcct gcaccggac agctgtgtca ccatgtgggt tctggttgtc ttcctcaccc       60
tgtccgtgac gtggattggc gctgcacccc tcatcctgtc tcggattgtg ggaggctggg      120
agtgcgagaa gcattcccaa ccctggcagg tgcttgtggc ctctcgtggc agggcagtct      180
gcgggggtgt tctggtgcac cccagtgggt cctcacagc tgcccactgc atcaggagca      240
acagcgtgat cttgctgggt cggcacaacc cgtattatcc tgaagacacg gccaggtgt      300
ttcaggtcag ccacagcttc ccacacccgc tctacaatat gagcctcctg aagaatcgat      360
acctcgggcc aggtgatgac tccagccacg acctcatgct gctccgcctg tcagagcctg      420
ccgagatcac agatgctgtg caggtcctgg acctgcccac ctgggagcca gagctgggga      480
ccacgtgcta cgcctcaggc tggggcagca tcgaaccaga ggaacacttg actccaaaga      540
aacttcagtg tgtggacctc catattattt ccaatgatgt gtgtgcgcaa gttcactctc      600
agaaggtgac caagttcatg ctgtgtgctg acgctggat gggcggcaaa agcacctgct      660
cgggtgattc tggggggccca ctggtctgtg acggtgtgct tcaaggtatc acgtcatggg      720
gcagtcaacc atgtgccctg ccccgaaggc cttccctgta caccaaggtg gtgcgttacc      780
ggaagtggat ccaggacacc atcatggcaa acccctgagc accccatcaa ctccctaatt      840
```

| | |
|---|---|
| gtagcgaaaa aaaaaagtcc acctcaagtt cttggcatca tttggctatt ctagacacca | 900 |
| ggcacttgga accttggaaa tgaccgggcc aaggctcaag cctcc | 945 |

<210> SEQ ID NO 3
<211> LENGTH: 944
<212> TYPE: DNA
<213> ORGANISM: Macaca fascicularis

<400> SEQUENCE: 3

| | |
|---|---|
| gctcaccgcc tgcacctgga cagctgtgtc accatgtggg ttctggttgt cttcctcacc | 60 |
| ctgtccgtga cgtggattgg cgctgcaccc ctcatcctgt ctcggattgt gggaggctgg | 120 |
| gagtgcgaga agcattccca accctggcag gtgcttgtgg cctctcatgg cagggcagtc | 180 |
| tgcgggggtg ttctggtgca cccccagtgg gtgctcacag ctgcccactg catcaggagc | 240 |
| cacagcgtga tcttgctggg tcggcacaac ccgtattatc ctgaagacac gggccaggtg | 300 |
| tttcaggtca gccacagctt cccacacccg ctctacaata tgagcctcct gaagaatcga | 360 |
| tacctcgggc aggtgatgac tccagccac gacctcatgc tgctccgcct gtcagagcct | 420 |
| gccgagatca cagatgctgt gcaggtcctg gacctgccca cctgggagcc agagctgggg | 480 |
| accacgtgct acgcctcagg ctggggcagc atcgaaccag aggaacactt gactccaaag | 540 |
| aaacttcagt gtgtggacct ccatattatt ccaatgatg tgtgtgcgca agttcactct | 600 |
| cagaaggtga ccaagttcat gctgtgtgct ggacgctgga tgggcggcaa aagcacctgc | 660 |
| tcgggtgatt ctgggggccc actggtctgt gacggtgtgc ttcaaggtat cacgtcatgg | 720 |
| ggcagtcaac catgtgccct gccccgaagg ccttccctgt acaccaaggt ggtgcgttac | 780 |
| cggaagtgga tccaggacac catcatggca aaccccctgag cacccatca actccctact | 840 |
| tgtagcgaaa aaaaaaatcc acctcaagtt ctggcatcat ttggctattc tagacaccag | 900 |
| gcacttggaa ccttggaaat gaccgggcca aggctcaagc ctcc | 944 |

<210> SEQ ID NO 4
<211> LENGTH: 940
<212> TYPE: DNA
<213> ORGANISM: primate

<400> SEQUENCE: 4

| | |
|---|---|
| gctcaccgcc tgcacctgga cagctgtgtc accatgtggg ttctggttgt cttcctcacc | 60 |
| ctgtccgtga cgtggattgg cgctgcaccc ctcatcctgt ctcggattgt gggaggctgg | 120 |
| gagtgcgaga agcattccca accctcaggt gcttgtggcc tctcgtggca gggcagtctg | 180 |
| cgggggtgtt ctggtgcacc ccagtgggt cctcacagct gcccactgca tcaggagcaa | 240 |
| cagcgtgatc ttgctgggtc ggcacaaccc gtattatcct gaagacacgg gccaggtgtt | 300 |
| tcaggtcagc cacagcttcc cacacccgct ctacaatatg agcctcctga gaatcgata | 360 |
| cctcgggcca ggtgatgact ccagccacga cctcatgctg ctccgcctgt cagagcctgc | 420 |
| cgagatcaca gatgctgtgc aggtcctgga cctgcccacc tgggagccag agctggggac | 480 |
| cacgtgctac gcctcaggct ggggcagcat cgaaccagag gaacacttga ctccaaagaa | 540 |
| acttcagtgt gtggacctcc atattatttc caatgatgtg tgtgcgcaag ttcactctca | 600 |
| gaaggtgacc aagttcatgc tgtgtgctgg acgctggatg gcggcaaaa gcacctgctc | 660 |
| gggtgattct gggggcccac tggtctgtga cggtgtgctt caaggtatca cgtcatgggg | 720 |
| cagtcaacca tgtgccctgc cccgaaggcc ttccctgtac accaaggtgg tgcgttaccg | 780 |
| gaagtggatc caggacacca tcatggcaaa ccccctgagca ccccatcaac tccctattgt | 840 | agcgaaaaaa aaaatccacc tcaagttctg catcatttgg ctattctaga caccaggcac    900 ttggaacctt ggaaatgacc gggccaaggc tcaagcctcc    940

<210> SEQ ID NO 5
<211> LENGTH: 261
<212> TYPE: PRT
<213> ORGANISM: Macaca mulatta

<400> SEQUENCE: 5

Met Trp Val Leu Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Ser Asn Ser Val Ile Leu Leu Gly Arg His Asn Pro
65                  70                  75                  80

Tyr Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
            100                 105                 110

Pro Gly Asp Asp Ser Ser His Asp Leu Met Leu Leu Arg Leu Ser Glu
        115                 120                 125

Pro Ala Glu Ile Thr Asp Ala Val Gln Val Leu Asp Leu Pro Thr Trp
    130                 135                 140

Glu Pro Glu Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Ile Ile Ser Asn Asp Val Cys Ala Gln Val His Ser Gln Lys Val
            180                 185                 190

Thr Glu Phe Met Leu Cys Ala Gly Ser Trp Met Gly Gly Lys Ser Thr
        195                 200                 205

Cys Ser Gly Asp Ser Gly Gly Pro Leu Val Cys Asp Gly Val Leu Gln
    210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Met Ala Asn Pro
            260

<210> SEQ ID NO 6
<211> LENGTH: 261
<212> TYPE: PRT
<213> ORGANISM: Homo sapiens

<400> SEQUENCE: 6

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

| Val | Cys | Gly | Gly | Val | Leu | Val | His | Pro | Gln | Trp | Val | Leu | Thr | Ala | Ala |
|---|---|---|---|---|---|---|---|---|---|---|---|---|---|---|---|
| | 50 | | | | 55 | | | | | 60 | | | | | |

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 7
<211> LENGTH: 786
<212> TYPE: DNA
<213> ORGANISM: Macaca mulatta

<400> SEQUENCE: 7

| | | |
|---|---|---|
| atgtgggttc tggttgtctt cctcaccctg tccgtgacgt ggattggcgc tgcacccctc | 60 |
| atcctgtctc ggattgtggg aggctgggag tgcgagaagc attcccaacc ctggcaggtg | 120 |
| cttgtggcct ctcgtggcag ggcagtctgt gggggtgttc tggtgcaccc ccagtgggtc | 180 |
| ctcacagctg cccactgcat caggagcaac agcgtgatct tgctgggtcg cacaacccg | 240 |
| tattatcctg aagacacggg ccaggtgttt caggtcagcc acagcttccc acaccgctc | 300 |
| tacaacatga gcctcctgaa gaatcgatac ctcgggccag tgatgactc cagccacgac | 360 |
| ctcatgctgc tccgcctgtc agagcctgcc gagatcacag atgctgtgca ggtcctggac | 420 |
| ctgcccacct gggagccaga gctggggacc acgtgctacg cctcaggctg ggcagcatc | 480 |
| gaaccggagg aacacttgac tccaagaaa cttcagtgtg tggacctcca tattatttcc | 540 |
| aatgatgtgt gtgcgcaagt tcactctcag aaggtgaccg agttcatgct gtgtgctgga | 600 |
| agctggatgg gcggcaaaag cacctgctcg ggtgattctg ggggcccact ggtctgtgac | 660 |
| ggtgtgcttc aaggtatcac gtcatggggc agtcaaccat gtgccctacc ccgaaggcct | 720 |
| tccctgtaca ccaaggtggt gcgttaccgg aagtggatcc aggacaccat catggcaaac | 780 |
| ccctga | 786 |

<210> SEQ ID NO 8

```
<211> LENGTH: 786
<212> TYPE: DNA
<213> ORGANISM: Homo sapiens
<300> PUBLICATION INFORMATION:
<308> DATABASE ACCESSION NUMBER: NM_001648
<309> DATABASE ENTRY DATE: 2002-04-04
<313> RELEVANT RESIDUES IN SEQ ID NO: (44)..(829)

<400> SEQUENCE: 8
atgtgggtcc cggttgtctt cctcaccctg tccgtgacgt ggattggtgc tgcaccctc      60
atcctgtctc ggattgtggg aggctgggag tgcgagaagc attcccaacc ctggcaggtg    120
cttgtggcct ctcgtggcag ggcagtctgc ggcggtgttc tggtgcaccc ccagtgggtc    180
ctcacagctg cccactgcat caggaacaaa agcgtgatct tgctgggtcg gcacagcctg    240
tttcatcctg aagacacagg ccaggtattt caggtcagcc acagcttccc acacccgctc    300
tacgatatga gcctcctgaa gaatcgattc ctcaggccag gtgatgactc cagccacgac    360
ctcatgctgc tccgcctgtc agagcctgcc gagctcacgg atgctgtgaa ggtcatggac    420
ctgcccaccc aggagccagc actggggacc acctgctacg cctcaggctg gggcagcatt    480
gaaccagagg agttcttgac cccaaagaaa cttcagtgtg tggacctcca tgttatttcc    540
aatgacgtgt gtgcgcaagt tcaccctcag aaggtgacca agttcatgct gtgtgctgga    600
cgctggacag ggggcaaaag cacctgctcg ggtgattctg ggggcccact tgtctgtaat    660
ggtgtgcttc aaggtatcac gtcatggggc agtgaaccat gtgccctgcc cgaaaggcct    720
tccctgtaca ccaaggtggt gcattaccgg aagtggatca aggacaccat cgtggccaac    780
ccctga                                                               786
```